US010687818B2

(12) United States Patent
Hodgkinson et al.

(10) Patent No.: US 10,687,818 B2
(45) Date of Patent: Jun. 23, 2020

(54) CIRCULAR STAPLER AND STAPLE LINE REINFORCMENT MATERIAL

(71) Applicant: Covidien LP, Mansfield, MA (US)

(72) Inventors: Gerald N. Hodgkinson, Guilford, CT (US); Richard Stevenson, Colchester, CT (US); Jennifer (Whiffen) Diederich, Eagle River, AK (US)

(73) Assignee: COVIDIEN LP, Mansfield, MA (US)

( * ) Notice: Subject to any disclaimer, the term of this patent is extended or adjusted under 35 U.S.C. 154(b) by 282 days.

(21) Appl. No.: 15/896,683

(22) Filed: Feb. 14, 2018

(65) Prior Publication Data

US 2018/0168654 A1 Jun. 21, 2018

Related U.S. Application Data

(63) Continuation of application No. 14/682,331, filed on Apr. 9, 2015, now abandoned, which is a continuation
(Continued)

(51) Int. Cl.
*A61B 17/10* (2006.01)
*A61B 17/072* (2006.01)
(Continued)

(52) U.S. Cl.
CPC .......... *A61B 17/105* (2013.01); *A61B 17/068* (2013.01); *A61B 17/07207* (2013.01); *A61B 17/07292* (2013.01); *A61B 17/1155* (2013.01); *B29C 65/08* (2013.01); *B29C 70/68* (2013.01); *A61B 2017/00526* (2013.01); *A61B 2017/07257* (2013.01); *A61B 2017/07271* (2013.01)

(58) Field of Classification Search
CPC ................ A61B 17/105; A61B 17/068; A61B 17/07207; A61B 17/07292; A61B 17/1155; A61B 2017/00526; A61B 2017/07257; A61B 2017/07271; B29C 65/08; B29C 70/68
USPC ...................... 227/175.1–182.1; 606/75, 219
See application file for complete search history.

(56) References Cited

U.S. PATENT DOCUMENTS 3,054,406 A 9/1962 Usher
3,124,136 A 3/1964 Usher
(Continued)

FOREIGN PATENT DOCUMENTS

CA 2282761 A1 9/1998
CN 101310680 A 11/2008
(Continued)

OTHER PUBLICATIONS

Extended European Search Report corresponding to Patent Application EP 12196912.5 dated Feb. 1, 2016.
(Continued)

*Primary Examiner* — Robert F Long
(74) *Attorney, Agent, or Firm* — Carter, DeLuca & Farrell LLP

(57) ABSTRACT

A surgical stapling instrument includes a staple cartridge assembly having a plurality of rows of staple receiving slots and an anvil assembly having a plurality of rows of staple forming recesses. The staple cartridge assembly, the anvil assembly, or both have one or more attachment members overmolded thereon. A staple line reinforcement material is attached to the attachment members.

10 Claims, 8 Drawing Sheets

Related U.S. Application Data of application No. 14/331,537, filed on Jul. 15, 2014, now Pat. No. 9,016,544, which is a continuation of application No. 13/094,893, filed on Apr. 27, 2011, now Pat. No. 8,789,737.

(51) Int. Cl.
*A61B 17/115* (2006.01)
*A61B 17/068* (2006.01)
*B29C 65/08* (2006.01)
*B29C 70/68* (2006.01)
*A61B 17/00* (2006.01)

(56) References Cited

U.S. PATENT DOCUMENTS

| | | |
|---|---|---|
| 3,499,591 A | 3/1970 | Green |
| 3,797,494 A | 3/1974 | Zaffaroni |
| 4,347,847 A | 9/1982 | Usher |
| 4,354,628 A | 10/1982 | Green |
| 4,452,245 A | 6/1984 | Usher |
| 4,527,724 A | 7/1985 | Chow et al. |
| 4,605,730 A | 8/1986 | Shalaby et al. |
| 4,655,221 A | 4/1987 | Devereux |
| 4,834,090 A | 5/1989 | Moore |
| 4,838,884 A | 6/1989 | Dumican et al. |
| 4,927,640 A | 5/1990 | Dahlinder et al. |
| 4,930,674 A | 6/1990 | Barak |
| 5,002,551 A | 3/1991 | Linsky et al. |
| 5,014,899 A | 5/1991 | Presty et al. |
| 5,040,715 A | 8/1991 | Green et al. |
| 5,065,929 A | 11/1991 | Schulze et al. |
| 5,112,496 A | 5/1992 | Dhawan et al. |
| 5,142,933 A | 9/1992 | Kelley |
| 5,205,459 A | 4/1993 | Brinkerhoff et al. |
| 5,263,629 A | 11/1993 | Trumbull et al. |
| 5,281,197 A | 1/1994 | Arias et al. |
| 5,308,576 A | 5/1994 | Green et al. |
| 5,314,471 A | 5/1994 | Brauker et al. |
| 5,344,454 A | 9/1994 | Clarke et al. |
| 5,392,979 A | 2/1995 | Green et al. |
| 5,397,324 A | 3/1995 | Carroll et al. |
| 5,405,072 A | 4/1995 | Zlock et al. |
| 5,425,745 A | 6/1995 | Green et al. |
| 5,441,193 A | 8/1995 | Gravener |
| 5,441,507 A | 8/1995 | Wilk |
| 5,443,198 A | 8/1995 | Viola et al. |
| 5,468,253 A | 11/1995 | Bezwada et al. |
| 5,503,638 A | 4/1996 | Cooper et al. |
| 5,542,594 A | 8/1996 | McKean et al. |
| 5,549,628 A | 8/1996 | Cooper et al. |
| 5,575,803 A | 11/1996 | Cooper et al. |
| 5,645,915 A | 7/1997 | Kranzler et al. |
| 5,653,756 A | 8/1997 | Clarke et al. |
| 5,683,809 A | 11/1997 | Freeman et al. |
| 5,690,675 A | 11/1997 | Sawyer et al. |
| 5,702,409 A | 12/1997 | Rayburn et al. |
| 5,752,965 A | 5/1998 | Francis et al. |
| 5,762,256 A | 6/1998 | Mastri et al. |
| 5,766,188 A | 6/1998 | Igaki |
| 5,769,892 A | 6/1998 | Kingwell |
| 5,782,396 A | 7/1998 | Mastri et al. |
| 5,799,857 A | 9/1998 | Robertson et al. |
| 5,810,855 A | 9/1998 | Rayburn et al. |
| 5,814,057 A | 9/1998 | Oi et al. |
| 5,833,695 A | 11/1998 | Yoon |
| 5,843,096 A | 12/1998 | Igaki et al. |
| 5,871,135 A | 2/1999 | Williamson, IV et al. |
| 5,895,412 A | 4/1999 | Tucker |
| 5,902,312 A | 5/1999 | Frater et al. |
| 5,908,427 A | 6/1999 | McKean et al. |
| 5,915,616 A | 6/1999 | Viola et al. |
| 5,931,847 A | 8/1999 | Bittner et al. |
| 5,957,363 A | 9/1999 | Heck |
| 5,964,774 A | 10/1999 | McKean et al. |
| 5,997,895 A | 12/1999 | Narotam et al. |
| 6,019,791 A | 2/2000 | Wood |
| 6,030,392 A | 2/2000 | Dakov |
| 6,032,849 A | 3/2000 | Mastri et al. |
| 6,045,560 A | 4/2000 | McKean et al. |
| 6,063,097 A | 5/2000 | Oi et al. |
| 6,080,169 A | 6/2000 | Turtel |
| 6,099,551 A | 8/2000 | Gabbay |
| 6,149,667 A | 11/2000 | Hovland et al. |
| 6,155,265 A | 12/2000 | Hammerslag |
| 6,210,439 B1 | 4/2001 | Firmin et al. |
| 6,214,020 B1 | 4/2001 | Mulhauser et al. |
| 6,241,139 B1 | 6/2001 | Milliman et al. |
| 6,258,107 B1 | 7/2001 | Balazs et al. |
| 6,267,772 B1 | 7/2001 | Mulhauser et al. |
| 6,270,530 B1 | 8/2001 | Eldridge et al. |
| 6,273,897 B1 | 8/2001 | Dalessandro et al. |
| 6,280,453 B1 | 8/2001 | Kugel et al. |
| 6,299,631 B1 | 10/2001 | Shalaby |
| 6,312,457 B1 | 11/2001 | DiMatteo et al. |
| 6,312,474 B1 | 11/2001 | Francis et al. |
| 6,325,810 B1 | 12/2001 | Hamilton et al. |
| 6,398,797 B2 | 6/2002 | Bombard et al. |
| 6,436,030 B2 | 8/2002 | Rehil |
| 6,454,780 B1 | 9/2002 | Wallace |
| 6,461,368 B2 | 10/2002 | Fogarty et al. |
| 6,503,257 B2 | 1/2003 | Grant et al. |
| 6,514,283 B2 | 2/2003 | DiMatteo et al. |
| 6,517,566 B1 | 2/2003 | Hovland et al. |
| 6,551,356 B2 | 4/2003 | Rousseau |
| 6,568,398 B2 | 5/2003 | Cohen |
| 6,592,597 B2 | 7/2003 | Grant et al. |
| 6,610,006 B1 | 8/2003 | Amid et al. |
| 6,638,285 B2 | 10/2003 | Gabbay |
| 6,652,594 B2 | 11/2003 | Francis et al. |
| 6,656,193 B2 | 12/2003 | Grant et al. |
| 6,669,735 B1 | 12/2003 | Pelissier |
| 6,677,258 B2 | 1/2004 | Carroll et al. |
| 6,685,714 B2 | 2/2004 | Rousseau |
| 6,704,210 B1 | 3/2004 | Myers |
| 6,723,114 B2 | 4/2004 | Shalaby |
| 6,726,706 B2 | 4/2004 | Dominguez |
| 6,736,823 B2 | 5/2004 | Darois et al. |
| 6,736,854 B2 | 5/2004 | Vadurro et al. |
| 6,746,458 B1 | 6/2004 | Cloud |
| 6,773,458 B1 | 8/2004 | Brauker et al. |
| 6,927,315 B1 | 8/2005 | Heinecke et al. |
| 7,025,772 B2 | 4/2006 | Gellman et al. |
| 7,128,748 B2 | 10/2006 | Mooradian et al. |
| 7,147,138 B2 | 12/2006 | Shelton, IV |
| 7,179,268 B2 | 2/2007 | Roy et al. |
| 7,210,810 B1 | 5/2007 | Iversen et al. |
| 7,434,717 B2 | 10/2008 | Shelton, IV et al. |
| 7,438,209 B1 | 10/2008 | Hess et al. |
| 7,547,312 B2 | 6/2009 | Bauman et al. |
| 7,559,937 B2 | 7/2009 | de la Torre et al. |
| 7,604,151 B2 | 10/2009 | Hess et al. |
| 7,665,646 B2 | 2/2010 | Prommersberger |
| 7,669,747 B2 | 3/2010 | Weisenburgh, II et al. |
| 7,717,313 B2 | 5/2010 | Criscuolo et al. |
| 7,722,642 B2 | 5/2010 | Williamson, IV et al. |
| 7,744,627 B2 | 6/2010 | Orban, III et al. |
| 7,776,060 B2 | 8/2010 | Mooradian et al. |
| 7,789,889 B2 | 9/2010 | Zubik et al. |
| 7,793,813 B2 | 9/2010 | Bettuchi |
| 7,799,026 B2 | 9/2010 | Schechter et al. |
| 7,823,592 B2 | 11/2010 | Bettuchi et al. |
| 7,845,533 B2 | 12/2010 | Marczyk et al. |
| 7,845,536 B2 | 12/2010 | Viola et al. |
| 7,846,149 B2 | 12/2010 | Jankowski |
| 7,909,224 B2 | 3/2011 | Prommersberger |
| 7,938,307 B2 | 5/2011 | Bettuchi |
| 7,950,561 B2 | 5/2011 | Aranyi |
| 7,951,166 B2 | 5/2011 | Orban, III et al. |
| 7,967,179 B2 | 6/2011 | Olson et al. |
| 7,988,027 B2 | 8/2011 | Olson et al. |
| 8,011,550 B2 | 9/2011 | Aranyi et al. |
| 8,016,177 B2 | 9/2011 | Bettuchi et al. |
| 8,016,178 B2 | 9/2011 | Olson et al. |

(56) References Cited

U.S. PATENT DOCUMENTS

| | | |
|---|---|---|
| 8,025,199 B2 | 9/2011 | Whitman et al. |
| 8,028,883 B2 | 10/2011 | Stopek |
| 8,033,983 B2 | 10/2011 | Chu et al. |
| 8,062,330 B2 | 11/2011 | Prommersberger et al. |
| 8,083,119 B2 | 12/2011 | Prommersberger |
| 8,123,766 B2 | 2/2012 | Bauman et al. |
| 8,123,767 B2 | 2/2012 | Bauman et al. |
| 8,127,975 B2 | 3/2012 | Olson et al. |
| 8,133,336 B2 | 3/2012 | Kettlewell et al. |
| 8,133,559 B2 | 3/2012 | Lee et al. |
| 8,146,791 B2 | 4/2012 | Bettuchi et al. |
| 8,157,149 B2 | 4/2012 | Olson et al. |
| 8,157,151 B2 | 4/2012 | Ingmanson et al. |
| 8,167,895 B2 | 5/2012 | D'Agostino et al. |
| 8,192,460 B2 | 6/2012 | Orban, III et al. |
| 8,210,414 B2 | 7/2012 | Bettuchi et al. |
| 8,225,799 B2 | 7/2012 | Bettuchi |
| 8,225,981 B2 | 7/2012 | Criscuolo et al. |
| 8,231,043 B2 | 7/2012 | Tarinelli et al. |
| 8,235,273 B2 | 8/2012 | Olson et al. |
| 8,245,901 B2 | 8/2012 | Stopek |
| 8,256,654 B2 | 9/2012 | Bettuchi et al. |
| 8,257,391 B2 | 9/2012 | Orban, III et al. |
| 8,276,800 B2 | 10/2012 | Bettuchi |
| 8,286,849 B2 | 10/2012 | Bettuchi |
| 8,308,042 B2 | 11/2012 | Aranyi |
| 8,308,045 B2 | 11/2012 | Bettuchi et al. |
| 8,308,046 B2 | 11/2012 | Prommersberger |
| 8,312,885 B2 | 11/2012 | Bettuchi et al. |
| 8,313,014 B2 | 11/2012 | Bettuchi |
| 8,322,590 B2 | 12/2012 | Patel et al. |
| 8,348,126 B2 | 1/2013 | Olson et al. |
| 8,348,130 B2 | 1/2013 | Shah et al. |
| 8,365,972 B2 | 2/2013 | Aranyi et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,393,514 B2 | 3/2013 | Shelton, IV et al. |
| 8,393,517 B2 | 3/2013 | Milo |
| 8,408,440 B2 | 4/2013 | Olson et al. |
| 8,413,871 B2 | 4/2013 | Racenet et al. |
| 8,424,742 B2 | 4/2013 | Bettuchi |
| 8,453,652 B2 | 6/2013 | Stopek |
| 8,453,904 B2 | 6/2013 | Eskaros et al. |
| 8,453,909 B2 | 6/2013 | Olson et al. |
| 8,453,910 B2 | 6/2013 | Bettuchi et al. |
| 8,464,925 B2 | 6/2013 | Hull et al. |
| 8,474,677 B2 | 7/2013 | Woodard, Jr. et al. |
| 8,479,968 B2 | 7/2013 | Hodgkinson et al. |
| 8,485,414 B2 | 7/2013 | Criscuolo et al. |
| 8,496,683 B2 | 7/2013 | Prommersberger et al. |
| 8,511,533 B2 | 8/2013 | Viola et al. |
| 8,512,402 B2 | 8/2013 | Marczyk et al. |
| 8,529,600 B2 | 9/2013 | Woodard, Jr. et al. |
| 8,540,131 B2 | 9/2013 | Swayze |
| 8,551,138 B2 | 10/2013 | Orban, III et al. |
| 8,556,918 B2 | 10/2013 | Bauman et al. |
| 8,561,873 B2 | 10/2013 | Ingmanson et al. |
| 8,579,990 B2 | 11/2013 | Priewe |
| 8,584,920 B2 | 11/2013 | Hodgkinson |
| 8,590,762 B2 | 11/2013 | Hess et al. |
| 8,616,430 B2 | 12/2013 | (Prommersberger) Stopek et al. |
| 8,631,989 B2 | 1/2014 | Aranyi et al. |
| 8,668,129 B2 | 3/2014 | Olson |
| 8,684,250 B2 | 4/2014 | Bettuchi et al. |
| 8,789,737 B2 | 7/2014 | Hodgkinson et al. |
| 8,814,888 B2 | 8/2014 | Sgro |
| 8,857,694 B2 | 10/2014 | Shelton, IV et al. |
| 8,864,009 B2 | 10/2014 | Shelton, IV et al. |
| 8,920,443 B2 | 12/2014 | Hiles et al. |
| 8,956,390 B2 * | 2/2015 | Shah ................ A61B 17/07207 606/213 |
| 9,016,544 B2 | 4/2015 | Hodgkinson et al. |
| 9,027,817 B2 | 5/2015 | Milliman et al. |
| 9,107,665 B2 * | 8/2015 | Hodgkinson .... A61B 17/07292 |
| 9,186,140 B2 | 11/2015 | Hiles et al. |
| 9,186,144 B2 | 11/2015 | Stevenson et al. |
| 9,192,378 B2 | 11/2015 | Aranyi et al. |
| 9,192,379 B2 | 11/2015 | Aranyi et al. |
| 9,192,380 B2 | 11/2015 | (Tarinelli) Racenet et al. |
| 9,192,383 B2 | 11/2015 | Milliman |
| 9,192,384 B2 | 11/2015 | Bettuchi |
| 9,198,660 B2 | 12/2015 | Hodgkinson |
| 9,198,663 B1 | 12/2015 | Marczyk et al. |
| 9,204,881 B2 | 12/2015 | Penna |
| 9,220,504 B2 | 12/2015 | Viola et al. |
| 9,226,754 B2 | 1/2016 | D'Agostino et al. |
| 9,237,892 B2 | 1/2016 | Hodgkinson |
| 9,237,893 B2 | 1/2016 | Carter et al. |
| 9,277,922 B2 | 3/2016 | Carter et al. |
| 9,295,466 B2 | 3/2016 | Hodgkinson et al. |
| 9,326,773 B2 | 5/2016 | Casasanta, Jr. et al. |
| 9,328,111 B2 | 5/2016 | Zhou et al. |
| 9,345,479 B2 | 5/2016 | (Tarinelli) Racenet et al. |
| 9,351,729 B2 | 5/2016 | Orban, III et al. |
| 9,351,731 B2 | 5/2016 | Carter et al. |
| 9,351,732 B2 | 5/2016 | Hodgkinson |
| 9,358,005 B2 | 6/2016 | Shelton, IV et al. |
| 9,364,229 B2 | 6/2016 | D'Agostino et al. |
| 9,364,234 B2 | 6/2016 | (Prommersberger) Stopek et al. |
| 9,393,018 B2 * | 7/2016 | Wang ................ A61B 17/068 |
| 9,402,627 B2 | 8/2016 | Stevenson et al. |
| 9,414,839 B2 | 8/2016 | Penna |
| 9,433,412 B2 | 9/2016 | Bettuchi et al. |
| 9,433,413 B2 | 9/2016 | Stopek |
| 9,433,420 B2 | 9/2016 | Hodgkinson |
| 9,445,812 B2 | 9/2016 | Olson et al. |
| 9,445,817 B2 | 9/2016 | Bettuchi |
| 9,486,215 B2 | 11/2016 | Olson et al. |
| 9,504,470 B2 | 11/2016 | Milliman |
| 9,572,576 B2 | 2/2017 | Hodgkinson et al. |
| 9,597,077 B2 | 3/2017 | Hodgkinson |
| 9,610,080 B2 | 4/2017 | Whitfield et al. |
| 9,622,745 B2 | 4/2017 | Ingmanson et al. |
| 9,629,626 B2 | 4/2017 | Soltz et al. |
| 9,655,620 B2 | 5/2017 | Prescott et al. |
| 9,675,351 B2 | 6/2017 | Hodgkinson et al. |
| 9,681,936 B2 | 6/2017 | Hodgkinson et al. |
| 9,693,772 B2 | 7/2017 | Ingmanson et al. |
| 9,775,617 B2 | 10/2017 | Carter et al. |
| 9,775,618 B2 | 10/2017 | Bettuchi et al. |
| 9,782,173 B2 | 10/2017 | Mozdzierz |
| 9,844,378 B2 | 12/2017 | Casasanta et al. |
| 9,931,116 B2 | 4/2018 | Racenet et al. |
| 10,022,125 B2 | 7/2018 | (Prommersberger) Stopek et al. |
| 10,098,639 B2 | 10/2018 | Hodgkinson |
| 10,111,659 B2 | 10/2018 | Racenet et al. |
| 10,154,840 B2 | 12/2018 | Viola et al. |
| 2002/0016626 A1 | 2/2002 | DiMatteo et al. |
| 2002/0019187 A1 | 2/2002 | Carroll et al. |
| 2002/0028243 A1 | 3/2002 | Masters |
| 2002/0052622 A1 | 5/2002 | Rousseau |
| 2002/0091397 A1 | 7/2002 | Chen |
| 2002/0133236 A1 | 9/2002 | Rousseau |
| 2002/0138152 A1 | 9/2002 | Francis et al. |
| 2002/0151911 A1 | 10/2002 | Gabbay |
| 2002/0165559 A1 | 11/2002 | Grant et al. |
| 2002/0165562 A1 | 11/2002 | Grant et al. |
| 2002/0165563 A1 | 11/2002 | Grant et al. |
| 2002/0177859 A1 | 11/2002 | Monassevitch et al. |
| 2003/0065345 A1 | 4/2003 | Weadock |
| 2003/0065346 A1 | 4/2003 | Evens et al. |
| 2003/0083676 A1 | 5/2003 | Wallace |
| 2003/0088256 A1 | 5/2003 | Conston et al. |
| 2003/0105510 A1 | 6/2003 | DiMatteo et al. |
| 2003/0114866 A1 | 6/2003 | Ulmsten et al. |
| 2003/0120284 A1 | 6/2003 | Palacios et al. |
| 2003/0125676 A1 | 7/2003 | Swenson et al. |
| 2003/0167064 A1 | 9/2003 | Whayne |
| 2003/0181927 A1 | 9/2003 | Wallace |
| 2003/0183671 A1 | 10/2003 | Mooradian et al. |
| 2003/0196668 A1 | 10/2003 | Harrison et al. |
| 2003/0208231 A1 | 11/2003 | Williamson et al. |
| 2004/0034377 A1 | 2/2004 | Sharkawy et al. |

(56) References Cited

U.S. PATENT DOCUMENTS

| | | |
|---|---|---|
| 2004/0092912 A1 | 5/2004 | Jinno et al. |
| 2004/0092960 A1 | 5/2004 | Abrams et al. |
| 2004/0093029 A1 | 5/2004 | Zubik et al. |
| 2004/0107006 A1 | 6/2004 | Francis et al. |
| 2004/0116945 A1 | 6/2004 | Sharkawy et al. |
| 2004/0131418 A1 | 7/2004 | Budde et al. |
| 2004/0142621 A1 | 7/2004 | Carroll et al. |
| 2004/0172048 A1 | 9/2004 | Browning |
| 2004/0209059 A1 | 10/2004 | Foss |
| 2004/0215214 A1 | 10/2004 | Crews et al. |
| 2004/0215219 A1 | 10/2004 | Eldridge et al. |
| 2004/0215221 A1 | 10/2004 | Suyker et al. |
| 2004/0232201 A1 | 11/2004 | Wenchell et al. |
| 2004/0254590 A1 | 12/2004 | Hoffman et al. |
| 2004/0260315 A1 | 12/2004 | Dell et al. |
| 2005/0002981 A1 | 1/2005 | Lahtinen et al. |
| 2005/0021026 A1 | 1/2005 | Baily |
| 2005/0021053 A1 | 1/2005 | Heinrich |
| 2005/0021085 A1 | 1/2005 | Abrams et al. |
| 2005/0059996 A1 | 3/2005 | Bauman et al. |
| 2005/0059997 A1 | 3/2005 | Bauman et al. |
| 2005/0070929 A1 | 3/2005 | Dalessandro et al. |
| 2005/0118435 A1 | 6/2005 | DeLucia et al. |
| 2005/0143756 A1 | 6/2005 | Jankowski |
| 2005/0149073 A1 | 7/2005 | Arani et al. |
| 2005/0228446 A1 | 10/2005 | Mooradian et al. |
| 2005/0245965 A1 | 11/2005 | Orban, III et al. |
| 2005/0283256 A1 | 12/2005 | Sommerich et al. |
| 2006/0004407 A1 | 1/2006 | Hiles et al. |
| 2006/0025816 A1 | 2/2006 | Shelton |
| 2006/0085030 A1 | 4/2006 | Bettuchi et al. |
| 2006/0085034 A1 | 4/2006 | Bettuchi |
| 2006/0135992 A1 | 6/2006 | Bettuchi et al. |
| 2006/0135995 A1 | 6/2006 | Ruff et al. |
| 2006/0173470 A1 | 8/2006 | Oray et al. |
| 2006/0178683 A1 | 8/2006 | Shimoji et al. |
| 2006/0190027 A1 | 8/2006 | Downey |
| 2006/0212050 A1 | 9/2006 | D'Agostino et al. |
| 2006/0219752 A1 | 10/2006 | Arad et al. |
| 2006/0271104 A1 | 11/2006 | Viola et al. |
| 2007/0026031 A1 | 2/2007 | Bauman et al. |
| 2007/0034669 A1 | 2/2007 | de la Torre et al. |
| 2007/0049953 A2 | 3/2007 | Shimoji et al. |
| 2007/0123839 A1 | 5/2007 | Rousseau et al. |
| 2007/0179528 A1 | 8/2007 | Soltz et al. |
| 2007/0203509 A1 | 8/2007 | Bettuchi |
| 2007/0203510 A1 | 8/2007 | Bettuchi |
| 2007/0246505 A1 | 10/2007 | Pace-Floridia et al. |
| 2008/0009811 A1 | 1/2008 | Cantor |
| 2008/0029570 A1 | 2/2008 | Shelton et al. |
| 2008/0082126 A1 | 4/2008 | Murray et al. |
| 2008/0110959 A1 | 5/2008 | Orban et al. |
| 2008/0125812 A1 | 5/2008 | Zubik et al. |
| 2008/0140115 A1 | 6/2008 | Stopek |
| 2008/0161831 A1 | 7/2008 | Bauman et al. |
| 2008/0161832 A1 | 7/2008 | Bauman et al. |
| 2008/0169327 A1 | 7/2008 | Shelton et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0200949 A1 | 8/2008 | Hiles et al. |
| 2008/0216855 A1 | 9/2008 | Nasca |
| 2008/0290134 A1 | 11/2008 | Bettuchi et al. |
| 2008/0308608 A1 | 12/2008 | Prommersberger |
| 2008/0314960 A1 | 12/2008 | Marczyk et al. |
| 2009/0001121 A1 | 1/2009 | Hess et al. |
| 2009/0001122 A1 | 1/2009 | Prommersberger et al. |
| 2009/0001123 A1 | 1/2009 | Morgan et al. |
| 2009/0001124 A1 | 1/2009 | Hess et al. |
| 2009/0001125 A1 | 1/2009 | Hess et al. |
| 2009/0001126 A1 | 1/2009 | Hess et al. |
| 2009/0001128 A1 | 1/2009 | Weisenburgh, II et al. |
| 2009/0001130 A1 | 1/2009 | Hess et al. |
| 2009/0005808 A1 | 1/2009 | Hess et al. |
| 2009/0030452 A1 | 1/2009 | Bauman et al. |
| 2009/0031842 A1 | 2/2009 | Kawai et al. |
| 2009/0043334 A1 | 2/2009 | Bauman et al. |
| 2009/0076510 A1 | 3/2009 | Bell et al. |
| 2009/0076528 A1 | 3/2009 | Sgro |
| 2009/0078739 A1 | 3/2009 | Viola |
| 2009/0095791 A1 | 4/2009 | Eskaros et al. |
| 2009/0095792 A1 | 4/2009 | Bettuchi |
| 2009/0120994 A1 | 5/2009 | Murray et al. |
| 2009/0134200 A1 | 5/2009 | Tarinelli et al. |
| 2009/0206125 A1 | 8/2009 | Huitema et al. |
| 2009/0206126 A1 | 8/2009 | Huitema et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0206143 A1 | 8/2009 | Huitema et al. |
| 2009/0218384 A1 | 9/2009 | Aranyi |
| 2009/0277947 A1 | 11/2009 | Viola |
| 2009/0287230 A1 | 11/2009 | D'Agostino et al. |
| 2010/0012704 A1 | 1/2010 | Tarinelli Racenet et al. |
| 2010/0016855 A1 | 1/2010 | Ramstein et al. |
| 2010/0065606 A1 | 3/2010 | Stopek |
| 2010/0065607 A1 | 3/2010 | Orban, III et al. |
| 2010/0072254 A1 | 3/2010 | Aranyi et al. |
| 2010/0147921 A1 | 6/2010 | Olson |
| 2010/0147922 A1 | 6/2010 | Olson |
| 2010/0147923 A1 | 6/2010 | D'Agostino et al. |
| 2010/0174253 A1 | 7/2010 | Cline et al. |
| 2010/0243707 A1 | 9/2010 | Olson et al. |
| 2010/0243708 A1 | 9/2010 | Aranyi et al. |
| 2010/0243711 A1 | 9/2010 | Olson et al. |
| 2010/0249805 A1 | 9/2010 | Olson et al. |
| 2010/0264195 A1 | 10/2010 | Bettuchi |
| 2010/0282815 A1 | 11/2010 | Bettuchi et al. |
| 2010/0331859 A1 | 12/2010 | Omori |
| 2011/0024476 A1 | 2/2011 | Bettuchi et al. |
| 2011/0024481 A1 | 2/2011 | Bettuchi et al. |
| 2011/0034910 A1 | 2/2011 | Ross et al. |
| 2011/0036894 A1 | 2/2011 | Bettuchi |
| 2011/0042442 A1 | 2/2011 | Viola et al. |
| 2011/0046650 A1 | 2/2011 | Bettuchi |
| 2011/0057016 A1 | 3/2011 | Bettuchi |
| 2011/0087279 A1 | 4/2011 | Shah et al. |
| 2011/0089220 A1 | 4/2011 | Ingmanson et al. |
| 2011/0125138 A1 | 5/2011 | Malinouskas et al. |
| 2011/0166673 A1 | 7/2011 | Patel et al. |
| 2011/0278346 A1 | 11/2011 | Hull et al. |
| 2011/0278347 A1 | 11/2011 | Olson et al. |
| 2012/0080484 A1 | 4/2012 | Morgan et al. |
| 2012/0145767 A1 | 6/2012 | Shah et al. |
| 2012/0187179 A1 | 7/2012 | Gleiman |
| 2012/0228360 A1 | 9/2012 | Hodgkinson et al. |
| 2012/0241491 A1 | 9/2012 | Aldridge et al. |
| 2012/0253298 A1 | 10/2012 | Henderson et al. |
| 2012/0273547 A1 | 11/2012 | Hodgkinson et al. |
| 2012/0289979 A1 | 11/2012 | Eskaros et al. |
| 2013/0037596 A1 | 2/2013 | Bear et al. |
| 2013/0075446 A1 | 3/2013 | Wang et al. |
| 2013/0105548 A1 | 5/2013 | Hodgkinson et al. |
| 2013/0105553 A1 | 5/2013 | (Tarinelli) Racenet et al. |
| 2013/0112732 A1 | 5/2013 | Aranyi et al. |
| 2013/0112733 A1 | 5/2013 | Aranyi et al. |
| 2013/0146643 A1 | 6/2013 | Schmid et al. |
| 2013/0153633 A1 | 6/2013 | Casasanta, Jr. et al. |
| 2013/0153634 A1 | 6/2013 | Carter et al. |
| 2013/0153635 A1 | 6/2013 | Hodgkinson |
| 2013/0153638 A1 | 6/2013 | Carter et al. |
| 2013/0153639 A1 | 6/2013 | Hodgkinson et al. |
| 2013/0153640 A1 | 6/2013 | Hodgkinson |
| 2013/0181031 A1 | 7/2013 | Olson et al. |
| 2013/0193186 A1 | 8/2013 | (Tarinelli) Racenet et al. |
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0209659 A1 | 8/2013 | Racenet et al. |
| 2013/0214030 A1 | 8/2013 | Aronhalt et al. |
| 2013/0221062 A1 | 8/2013 | Hodgkinson |

(56) References Cited

U.S. PATENT DOCUMENTS

| | | |
|---|---|---|
| 2013/0221063 A1 | 8/2013 | Aronhalt et al. |
| 2013/0221064 A1 | 8/2013 | Aronhalt et al. |
| 2013/0221065 A1 | 8/2013 | Aronhalt et al. |
| 2013/0240600 A1 | 9/2013 | Bettuchi |
| 2013/0240601 A1 | 9/2013 | Bettuchi et al. |
| 2013/0240602 A1 | 9/2013 | Stopek |
| 2013/0256373 A1 | 10/2013 | Schmid et al. |
| 2013/0277411 A1 | 10/2013 | Hodgkinson et al. |
| 2013/0306707 A1 | 11/2013 | Viola et al. |
| 2013/0310873 A1 | 11/2013 | Stopek (nee Prommersberger) et al. |
| 2013/0327807 A1 | 12/2013 | Olson et al. |
| 2014/0012317 A1 | 1/2014 | Orban et al. |
| 2014/0021242 A1 | 1/2014 | Hodgkinson et al. |
| 2014/0027490 A1 | 1/2014 | Marczyk et al. |
| 2014/0034704 A1 | 2/2014 | Ingmanson et al. |
| 2014/0048580 A1 | 2/2014 | Merchant et al. |
| 2014/0061280 A1 | 3/2014 | Ingmanson et al. |
| 2014/0061281 A1 | 3/2014 | Hodgkinson |
| 2014/0224686 A1 | 8/2014 | Aronhalt et al. |
| 2015/0001276 A1* | 1/2015 | Hodgkinson .... A61B 17/07292 227/180.1 |
| 2015/0133995 A1 | 5/2015 | Shelton, IV et al. |
| 2015/0231409 A1 | 8/2015 | Racenet et al. |
| 2015/0305743 A1 | 10/2015 | Casasanta et al. |
| 2015/0327864 A1 | 11/2015 | Hodgkinson et al. |
| 2016/0022268 A1 | 1/2016 | Prior |
| 2016/0045200 A1 | 2/2016 | Milliman |
| 2016/0058451 A1 | 3/2016 | (Tarinelli) Racenet et al. |
| 2016/0100834 A1 | 4/2016 | Viola et al. |
| 2016/0106430 A1 | 4/2016 | Carter et al. |
| 2016/0113647 A1 | 4/2016 | Hodgkinson |
| 2016/0128694 A1 | 5/2016 | Baxter, III et al. |
| 2016/0157857 A1 | 6/2016 | Hodgkinson et al. |
| 2016/0174988 A1 | 6/2016 | D'Agostino et al. |
| 2016/0206315 A1 | 7/2016 | Olson |
| 2016/0220257 A1 | 8/2016 | Casasanta et al. |
| 2016/0249923 A1 | 9/2016 | Hodgkinson et al. |
| 2016/0256166 A1 | 9/2016 | (Prommersberger) Stopek et al. |
| 2016/0270793 A1 | 9/2016 | Carter et al. |
| 2016/0310143 A1 | 10/2016 | Bettuchi |
| 2016/0338704 A1 | 11/2016 | Penna |
| 2016/0367252 A1 | 12/2016 | Olson et al. |
| 2016/0367253 A1 | 12/2016 | Hodgkinson |
| 2016/0367257 A1 | 12/2016 | Stevenson et al. |
| 2017/0042540 A1 | 2/2017 | Olson et al. |
| 2017/0049452 A1 | 2/2017 | Milliman |
| 2017/0119390 A1 | 5/2017 | Schellin et al. |
| 2017/0150967 A1 | 6/2017 | Hodgkinson et al. |
| 2017/0172575 A1 | 6/2017 | Hodgkinson |
| 2017/0231629 A1 | 8/2017 | Stopek et al. |
| 2017/0238931 A1 | 8/2017 | Prescott et al. |
| 2017/0281328 A1 | 10/2017 | Hodgkinson et al. |
| 2017/0296188 A1 | 10/2017 | Ingmanson et al. |
| 2017/0354415 A1 | 12/2017 | Casasanta, Jr. et al. |
| 2018/0125491 A1 | 5/2018 | Aranyi |
| 2018/0140301 A1 | 5/2018 | Milliman |
| 2018/0168654 A1 | 6/2018 | Hodgkinson et al. |
| 2018/0214147 A1 | 8/2018 | Merchant et al. |
| 2018/0229054 A1 | 8/2018 | Racenet et al. |
| 2018/0250000 A1 | 9/2018 | Hodgkinson et al. |
| 2018/0256164 A1 | 9/2018 | Aranyi |
| 2018/0296214 A1 | 10/2018 | Hodgkinson et al. |
| 2018/0310937 A1 | 11/2018 | (Prommersberger) Stopek et al. |
| 2019/0021734 A1 | 1/2019 | Hodgkinson |
| 2019/0059878 A1 | 2/2019 | (Tarinelli) Racenet et al. |
| 2019/0083087 A1 | 3/2019 | Viola et al. |

FOREIGN PATENT DOCUMENTS

| | | |
|---|---|---|
| CN | 101332110 A | 12/2008 |
| DE | 1602563 U | 3/1950 |
| DE | 1 99 24 311 A1 | 11/2000 |
| EP | 0327022 A2 | 8/1989 |
| EP | 0594148 A1 | 4/1994 |
| EP | 0667119 A1 | 8/1995 |
| EP | 1064883 A1 | 1/2001 |
| EP | 1256317 A2 | 11/2002 |
| EP | 1520525 A1 | 4/2005 |
| EP | 1621141 A2 | 2/2006 |
| EP | 1702570 A1 | 9/2006 |
| EP | 1759640 A2 | 3/2007 |
| EP | 1815804 A2 | 8/2007 |
| EP | 1825820 A1 | 8/2007 |
| EP | 1929958 A2 | 6/2008 |
| EP | 1994890 A1 | 11/2008 |
| EP | 2005894 A2 | 12/2008 |
| EP | 2005895 A2 | 12/2008 |
| EP | 2008595 A2 | 12/2008 |
| EP | 2090231 A1 | 8/2009 |
| EP | 2090244 A2 | 8/2009 |
| EP | 2090252 A2 | 8/2009 |
| EP | 2198787 A1 | 6/2010 |
| EP | 2236098 A2 | 10/2010 |
| EP | 2311386 A2 | 4/2011 |
| EP | 2462880 A2 | 6/2012 |
| EP | 2491867 A1 | 8/2012 |
| EP | 2517637 A1 | 10/2012 |
| EP | 2620106 A2 | 7/2013 |
| EP | 2630922 A1 | 8/2013 |
| EP | 2644125 A2 | 10/2013 |
| JP | 07124166 A | 5/1995 |
| JP | 2000166933 A | 6/2000 |
| JP | 2002202213 A | 7/2002 |
| WO | 9005489 A1 | 5/1990 |
| WO | 9516221 A1 | 6/1995 |
| WO | 9622055 A1 | 7/1996 |
| WO | 9701989 A1 | 1/1997 |
| WO | 9713463 A1 | 4/1997 |
| WO | 9817180 A1 | 4/1998 |
| WO | 98/38923 A1 | 9/1998 |
| WO | 9945849 A1 | 9/1999 |
| WO | 03082126 A1 | 10/2003 |
| WO | 03088845 A2 | 10/2003 |
| WO | 03094743 A1 | 11/2003 |
| WO | 03105698 A2 | 12/2003 |
| WO | 2005079675 A2 | 9/2005 |
| WO | 2006023578 A2 | 3/2006 |
| WO | 2006044490 A2 | 4/2006 |
| WO | 2006083748 A1 | 8/2006 |
| WO | 2007121579 A1 | 11/2007 |
| WO | 2008057281 A2 | 5/2008 |
| WO | 2008109125 A1 | 9/2008 |
| WO | 2010075298 A2 | 7/2010 |
| WO | 2011143183 A2 | 11/2011 |
| WO | 2012044848 A1 | 4/2012 |

OTHER PUBLICATIONS

Chinese Second Office Action corresponding to Patent Application CN 201610279682.3 dated Aug. 8, 2018.

Chinese Second Office Action corresponding to Patent Application CN 201410588811.8 dated Aug. 27, 2018.

Extended European Search Report corresponding to Patent Application EP 18160809.2 dated Sep. 18, 2018.

Extended European Search Report corresponding to Patent Application EP 18192317.8 dated Dec. 20, 2018.

Extended European Search Report corresponding to Patent Application EP 18190154.7 dated Feb. 4, 2019.

Chinese First Office Action corresponding to Patent Application CN 201410588811.8 dated Dec. 5, 2017.

European Office Action corresponding to Patent Application EP 16 16 6367.9 dated Dec. 11, 2017.

Chinese First Office Action corresponding to Patent Application CN 201610279682.3 dated Jan. 10, 2018.

Japanese Office Action corresponding to Patent Application JP 2013-154561 dated Jan. 15, 2018.

Australian Examination Report No. 1 corresponding to Patent Application AU 2017225037 dated Jan. 23, 2018.

Japanese Office Action corresponding to Patent Application JP 2013-229471 dated May 1, 2018.

(56) References Cited

OTHER PUBLICATIONS

Canadian Office Action corresponding to Patent Application CA 2,790,743 dated May 14, 2018.
European Office Action corresponding to Patent Application EP 14 15 7195.0 dated Jun. 12, 2018.
Japanese Office Action corresponding to JP 2012-250058 dated Jun. 29, 2016.
European Office Action corresponding to EP 14 15 7997.9 dated Jun. 29, 2016.
Canadian Office Action corresponding to CA 2,712,617 dated Jun. 30, 2016.
Chinese First Office Action corresponding to CN 2013103036903 dated Jun. 30, 2016.
Australian Patent Examination Report No. 1 corresponding to AU 2012250278 dated Jul. 10, 2016.
Australian Patent Examination Report No. 1 corresponding to AU 2012244382 dated Jul. 10, 2016.
Japanese Office Action corresponding to 2012-255242 dated Jul. 26, 2016.
Japanese Office Action corresponding to JP 2012-268668 dated Jul. 27, 2016.
European Office Action corresponding to EP 14 15 2060.1 dated Aug. 4, 2016.
European Office Action corresponding to EP 15 15 2392.5 dated Aug. 8, 2016.
Japanese Office Action corresponding to JP 2013-003624 dated Aug. 25, 2016.
Australian Patent Examination Report No. 1 corresponding to AU 2012261752 dated Sep. 6, 2016.
Japanese Office Action corresponding to JP 2014-252703 dated Sep. 26, 2016.
European Office Action corresponding to EP 12 19 8776.2 dated Sep. 12, 2016.
Japanese Office Action corresponding to JP 2013-000321 dated Sep. 13, 2016.
Chinese Second Office Action corresponding to CN 201310353628.5 dated Sep. 26, 2016.
European Office Action corresponding to EP 12 15 2541.4 dated Sep. 27, 2016.
Australian Patent Examination Report No. 1 corresponding to AU 2012268923 dated Sep. 28, 2016.
Chinese First Office Action corresponding to CN 2013107068710 dated Dec. 16, 2016.
Chinese First Office Action corresponding to CN 201310646606.8 dated Dec. 23, 2016.
Japanese Office Action corresponding to JP 2013-000321 dated Jan. 4, 2017.
Extended European Search Report corresponding to EP 16 16 6367.9 dated Jan. 16, 2017.
Australian Examination Report No. 1 corresponding to AU 2013206777 dated Feb. 1, 2017.
Chinese Second Office Action corresponding to CN 2013103036903 dated Feb. 23, 2017.
Japanese Office Action corresponding to JP 2013-175379 dated Mar. 1, 2017.
Chinese First Office Action corresponding to CN 201410028462.4 dated Mar. 2, 2017.
Chinese First Office Action corresponding to CN 201410084070 dated Mar. 13, 2017.
Extended European Search Report corresponding to EP 16 19 6549.6 dated Mar. 17, 2017.
Japanese Office Action corresponding to JP 2013-147701 dated Mar. 21, 2017.
Australian Examination Report No. 1 corresponding to AU 2013206804 dated Mar. 21, 2017.
Australian Examination Report No. 1 corresponding to AU 2013211499 dated May 4, 2017.
Australian Examination Report No. 1 corresponding to AU 2014201008 dated May 23, 2017.
Chinese Second Office Action with English translation, dated Aug. 24, 2015, corresponding to Chinese Patent Application No. 201210129787.2; 19 pages.
International Search Report corresponding to European Application No. EP 11 18 8309.6, completed on Dec. 15, 2011 and dated Jan. 12, 2012; 3 pages.
International Search Report corresponding to European Application No. EP 12 15 2229.6, completed on Feb. 23, 2012 and dated Mar. 1, 2012; 4 pages.
International Search Report corresponding to European Application No. EP 12 15 0511.9, completed on Apr. 16, 2012 and dated Apr. 24, 2012; 7 pages.
International Search Report corresponding to European Application No. EP 12 15 2541.4, completed on Apr. 23, 2012 and dated May 3, 2012; 10 pages.
International Search Report corresponding to European Application No. EP 12 15 8861.0, completed on Jul. 17, 2012 and dated Jul. 24, 2012; 9 pages.
International Search Report corresponding to European Application No. EP 12 16 58785, completed on Jul. 24, 2012 and dated Aug. 6, 2012; 8 pages.
International Search Report corresponding to European Application No. EP 06 00 4598, completed on Jun. 22, 2006; 2 pages.
International Search Report corresponding to European Application No. EP 06 01 6962.0, completed on Jan. 3, 2007 and dated Jan. 11, 2007; 10 pages.
International Search Report corresponding to International Application No. PCT/US05/36740, completed on Feb. 20, 2007 and dated Mar. 23, 2007; 8 pages.
International Search Report corresponding to International Application No. PCT/US2008/002981, completed on Jun. 9, 2008 and dated Jun. 26, 2008; 2 pages.
International Search Report corresponding to European Application No. EP 08 25 1779, completed on Jul. 14, 2008 and dated Jul. 23, 2008; 5 pages.
International Search Report corresponding to European Application No. EP 08 25 1989.3, completed on Mar. 11, 2010 and dated Mar. 24, 2010; 3 pages.
International Search Report corresponding to European Application No. EP 10 25 0715.9, completed on Jun. 30, 2010 and dated Jul. 20, 2010; 3 pages.
International Search Report corresponding to European Application No. EP 05 80 4382.9, completed on Oct. 5, 2010 and dated Oct. 12, 2010; 3 pages.
International Search Report corresponding to European Application No. EP 10 25 1437.9, completed on Nov. 22, 2010 and dated Dec. 16, 2010; 3 pages.
International Search Report corresponding to European Application No. EP 09 25 2897.5, completed on Feb. 7, 2011 and dated Feb. 15, 2011; 3 pages.
International Search Report corresponding to European Application No. EP 10 25 0642.5, completed on Mar. 25, 2011 and dated Apr. 4, 2011; 4 pages.
Extended European Search Report corresponding to EP No. 12 19 1035.0, completed Jan. 11, 2013 and dated Jan. 18, 2013; 7 pages.
Extended European Search Report corresponding to EP No. 12 18 6175.1, completed Jan. 15, 2013 and dated Jan. 23, 2013; 7 pages.
Extended European Search Report corresponding to EP No. 12 19 1114.3, completed Jan. 23, 2013 and dated Jan. 31, 2013; 10 pages.
Extended European Search Report corresponding to EP No. 12 19 2224.9, completed Mar. 14, 2013 and dated Mar. 26, 2013; 8 pages.
Extended European Search Report corresponding to EP No. 12 19 6911.7, completed Apr. 18, 2013 and dated Apr. 24, 2013; 8 pages.
Extended European Search Report corresponding to EP 12 19 1035.0, completed Jan. 11, 2013 and dated Jan. 18, 2013; 7 pages.
Extended European Search Report corresponding to EP 12 19 6904.2, completed Mar. 28, 2013 and dated Jul. 26, 2013; 8 pages.
Extended European Search Report corresponding to EP12 19 8749.9, completed May 21, 2013 and dated May 31, 2013; 8 pages.
Extended European Search Report corresponding to EP 07 00 5842.5, completed May 13, 2013 and dated May 29, 2013; 7 pages.
Extended European Search Report corresponding to EP12 19 8776.2, completed May 16, 2013 and dated May 27, 2013; 8 pages.

(56) References Cited

OTHER PUBLICATIONS

Extended European Search Report corresponding to EP 13 15 6297.7, completed Jun. 4, 2013 and dated Jun. 13, 2013; 7 pages.
Extended European Search Report corresponding to EP 13 17 3985.6, completed Aug. 19, 2013 and dated Aug. 28, 2013; 6 pages.
Extended European Search Report corresponding to EP 13 17 3986.4, completed Aug. 20, 2013 and dated Aug. 29, 2013; 7 pages.
Extended European Search Report corresponding to EP 13 17 7437.4, completed Sep. 11, 2013 and dated Sep. 19, 2013; (6 pp).
Extended European Search Report corresponding to EP 13 17 7441.6, completed Sep. 11, 2013 and dated Sep. 19, 2013; (6 pp).
Extended European Search Report corresponding to EP 07 86 1534.1, completed Sep. 20, 2013 and dated Sep. 30, 2013; (5 pp).
Extended European Search Report corresponding to EP 13 18 3876.5, completed Oct. 14, 2013 and dated Oct. 24, 2013; (5 pp).
Extended European Search Report corresponding to EP 13 17 1856.1, completed Oct. 29, 2013 and dated Nov. 7, 2013; (8 pp).
Extended European Search Report corresponding to EP 13 18 0373.6, completed Oct. 31, 2013 and dated Nov. 13, 2013; (7 pp).
Extended European Search Report corresponding to EP 13 18 0881.8, completed Nov. 5, 2013 and dated Nov. 14, 2013; (6 pp).
Extended European Search Report corresponding to EP 13 17 6895.4, completed Nov. 29, 2013 and dated Dec. 12, 2013; (5 pp).
Extended European Search Report corresponding to EP 13 18 2911.1, completed Dec. 2, 2013 and dated Dec. 16, 2013; (8 pp).
Extended European Search Report corresponding to EP 10 25 1795.0, completed Dec. 11, 2013 and dated Dec. 20, 2013; (6 pp).
Extended European Search Report corresponding to EP 13 18 7911.6, completed Jan. 22, 2014 and dated Jan. 31, 2014; (8 pp).
International Search Report corresponding to European Application No. EP 12165609.4, completed on Jul. 5, 2012; 7 pages.
European Office Action corresponding to EP 15 17 4146.9 dated May 15, 2017.
Japanese Office Action corresponding to JP 2013-154561 dated May 23, 2017.
European Office Action corresponding to EP 12 19 4784.0 dated May 29, 2017.
Japanese Office Action corresponding to JP 2013-169083 dated May 31, 2017.
Australian Examination Report No. 1 corresponding to AU 2013213767 dated Jun. 29, 2017.
Australian Examination Report No. 2 corresponding to AU 2012261752 dated Jul. 7, 2017.
Australian Examination Report No. 1 corresponding to AU 2013266989 dated Jul. 10, 2017.
Extended European Search Report corresponding to EP 14 15 3609.4 dated Jul. 14, 2017.
Australian Examination Report No. 1 corresponding to AU 2013234418 dated Jul. 14, 2017.
Extended European Search Report corresponding to EP 14 15 3610.2 dated Jul. 17, 2017.
Australian Examination Report No. 1 corresponding to AU 2014200109 dated Jul. 20, 2017.
Australian Examination Report No. 1 corresponding to AU 2014200074 dated Jul. 20, 2017.
Japanese Office Action corresponding to JP 2013-250857 dated Aug. 17, 2017.
Japanese Office Action corresponding to JP 2013-229471 dated Aug. 17, 2017.
Australian Examination Report No. 1 corresponding to AU 2014200793 dated Sep. 2, 2017.
European Search Report corresponding to EP 17 17 8528.0 dated Oct. 13, 2017.
Australian Examination Report No. 1 corresponding to AU 2013234420 dated Oct. 24, 2017.
Japanese Office Action corresponding to JP 2013-175379 dated Oct. 20, 2017.
Japanese Office Action corresponding to JP 2013-147701 dated Oct. 27, 2017.
Extended European Search Report corresponding to EP 17 17 5656.2 dated Nov. 7, 2017.
Japanese Office Action corresponding to JP 2014-009738 dated Nov. 14, 2017.
European Office Action corresponding to EP 13 17 3986.4 dated Nov. 29, 2017.
Japanese Office Action corresponding to JP 2017-075975 dated Dec. 4, 2017.
European Office Action corresponding to EP 13 19 7958.5 dated Dec. 11, 2017.
Extended European Search Report corresponding to EP 14 15 2060.1 dated Aug. 14, 2015.
Chinese Notification of Reexamination corresponding to CN 201010517292.8 dated Jun. 2, 2015.
Japanese Office Action corresponding to JP 2014-216989 dated Sep. 11, 2015.
Canadian First Office Action corresponding to CA 2,686,105 dated Sep. 17, 2015.
Japanese Office Action corresponding to JP 2012-040188 dated Oct. 21, 2015.
European Communication corresponding to EP 13 17 6895.4 dated Nov. 5, 2015.
Chinese First Office Action corresponding to CN 201210544552 dated Nov. 23, 2015.
Chinese First Office Action corresponding to CN 201210545228 dated Nov. 30, 2015.
Extended European Search Report corresponding to EP 15 18 0491.1 dated Dec. 9, 2015.
Extended European Search Report corresponding to EP 15 18 3819.0 dated Dec. 11, 2015.
Canadian Office Action corresponding to CA 2,697,819 dated Jan. 6, 2016.
Canadian Office Action corresponding to CA 2,696,419 dated Jan. 14, 2016.
European Office Action corresponding to EP 12 19 8776.2 dated Jan. 19, 2016.
Extended European Search Report corresponding to EP 15 17 4146.9 dated Jan. 20, 2016.
Chinese First Office Action corresponding to CN 201310353628.5 dated Jan. 25, 2016.
Extended European Search Report corresponding to EP 12 19 6912.5 dated Feb. 1, 2016.
Japanese Office Action corresponding to JP 2012-098903 dated Feb. 22, 2016.
Extended European Search Report corresponding to EP 12 19 8753.1 dated Feb. 24, 2016.
Chinese First Office Action corresponding to CN 201410449019.4 dated Mar. 30, 2016.
Extended European Search Report corresponding to EP 16 15 0232.3 dated Apr. 12, 2016.
European Office Action corresponding to EP 11 18 3256.4 dated Apr. 20, 2016.
Australian Examination Report No. 1 corresponding to AU 2012244169 dated May 10, 2016.
European Office Action corresponding to EP 10 25 0715.9 dated May 12, 2016.
Chinese First Office Action corresponding to CN 201410778512.0 dated May 13, 2016.
Australian Examination Report No. 1 corresponding to AU 2012227358 dated May 16, 2016.
Japanese Office Action corresponding to JP 2012-040188 dated May 17, 2016.
Australian Examination Report No. 1 corresponding to AU 2012244380 dated May 20, 2016.
Australian Examination Report No. 1 corresponding to AU 2014227480 dated May 21, 2016.
Australian Examination Report No. 1 corresponding to AU 2012254977 dated May 30, 2016.
Extended European Search Report corresponding to EP 16 15 3647.9 dated Jun. 3, 2016.
European Communication, dated Aug. 5, 2016, corresponding to European Application No. 12 165 609.4; 4 pages.

(56) References Cited

OTHER PUBLICATIONS

European Office Action corresponding to EP 14 17 2681.0 dated May 13, 2016.
Chinese Office Action corresponding to CN 201210545228 dated Jun. 29, 2016.

\* cited by examiner

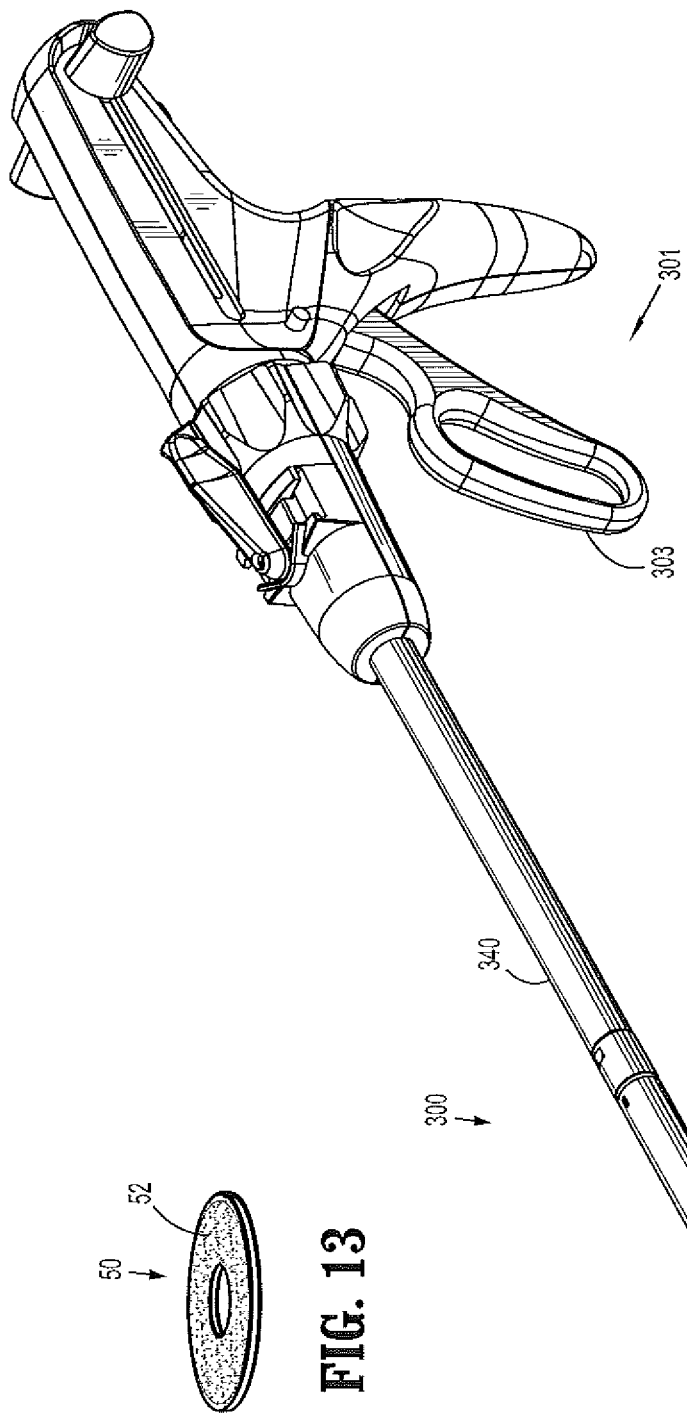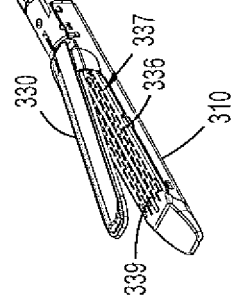

CIRCULAR STAPLER AND STAPLE LINE REINFORCMENT MATERIAL

CROSS REFERENCE TO RELATED APPLICATIONS

The present application is a Continuation Application claiming the benefit of and priority to U.S. patent application Ser. No. 14/682,331, filed on Apr. 9, 2015, which is a Continuation Application claiming the benefit of and priority to U.S. patent application Ser. No. 14/331,537, filed on Jul. 15, 2014 (now U.S. Pat. No. 9,016,544), which is a Continuation Application claiming the benefit of and priority to U.S. patent application Ser. No. 13/094,893, filed on Apr. 27, 2011 (now U.S. Pat. No. 8,789,737), the entire contents of each of which are incorporated herein by reference.

BACKGROUND

1. Technical Field

The present application relates to surgical stapling and staple line reinforcement materials. In particular, the staple line reinforcement material is attached to one or both tissue contacting surfaces of a surgical stapler utilizing a retainer.

2. Background

The use of staple line reinforcement materials, or buttresses, in conjunction with staplers is known. U.S. Pat. No. 5,542,594 to McKean et al., the disclosure of which is hereby incorporated by reference herein, discloses a surgical stapling apparatus with a biocompatible surgical fabric attached to the apparatus. The surgical fabric and staples are attached to body tissue by the stapling apparatus. Pins or clips secure the fabric to surfaces of the stapling apparatus.

U.S. Pat. No. 7,128,748 discloses a circular stapler and buttress. The buttress material is positioned on the staple cartridge of the stapler and on the anvil component of the stapler. The anvil buttress material has a cylindrical raised center portion adapted to fit the central recessed aperture of the anvil and the staple cartridge buttress has a cylindrical raised center portion adapted to fit a central recessed aperture in the cartridge component of the stapler.

U.S. Pat. No. 6,503,257 discloses an adhesive used to releasably attach a buttress material to clamping members of a stapler. The buttress material is releasably attached by the adhesive material.

There is a need for a staple line reinforcement material or buttress material attachment that does not complicate assembly or manufacturing, does not interfere with the operation of the surgical instrument, and securely attaches the material while allowing the material to be reliably released when desired.

SUMMARY

In an aspect of the present disclosure, a surgical stapling instrument comprises a staple cartridge assembly having a plurality of rows of staple receiving slots, an anvil assembly having an anvil member defining a plurality of rows of staple forming recesses. The staple cartridge assembly, the anvil assembly, or both, has one or more attachment members. A staple line reinforcement material is attached to the attachment members by ultrasonic welding.

In certain embodiments, the staple line reinforcement material defines perforations adjacent the attachment members. Such perforations can be useful to facilitate release of the buttress from the surgical stapling apparatus. In certain embodiments, the surgical stapling instrument is a circular stapler. The plurality of rows of staple receiving slots can be circular rows. Such staplers are useful in intestinal anastomosis procedures and other surgical procedures. The plurality of rows of staple forming recesses can be circular rows.

In certain embodiments, the one or more attachment members are formed on the anvil member by molding plastic. The one or more attachment members can be disposed on the anvil member; the anvil member is made of metal, whereas the attachment members can made from plastic.

In certain embodiments, the one or more attachment members are disposed on the staple cartridge assembly outwardly of the rows of staple receiving slots. The staple line reinforcement material can be attached to the one or more attachment members and define perforations adjacent the one or more attachment members. In this way, the staple line reinforcement material lifts away from the staple cartridge assembly, separating at the perforations. A margin of material remains on the staple cartridge assembly.

In another arrangement, the one or more attachment members are disposed on the anvil assembly outwardly of the rows of staple forming recesses. The staple line reinforcement material is attached to the one or more attachment members and defines perforations adjacent the one or more attachment members.

The anvil assembly may include a hub attached to the anvil member. The anvil assembly may include a shaft and further comprising a tubular body portion, the staple cartridge assembly being mountable in the tubular body portion; the tubular body portion has a rod, the shaft of the anvil assembly being attachable to the shaft. The surgical stapling instrument, in certain embodiments, comprises a handle assembly.

In another aspect of the present disclosure, a surgical stapling instrument comprises a staple cartridge assembly having a plurality of rows of staple receiving slots, an anvil assembly having a shaft and an anvil member; the anvil member defines a plurality of rows of staple forming recesses. A retainer is engaged to the shaft, and a staple line reinforcement material attached to the anvil assembly by the retainer.

The surgical stapling instrument can be a circular stapler. The plurality of rows of staple receiving slots can be circular rows, whereas the plurality of rows of staple forming recesses would be circular rows.

In certain embodiments, the retainer is circular in shape and has a central aperture for receiving the shaft. The retainer may be frictionally engaged with the shaft. For example, the retainer is formed of a material that has a coefficient of friction with the shaft, the coefficient of friction being selected so as to retain the retainer and the staple line reinforcement material on the shaft.

In certain embodiments, the retainer is secured to the shaft utilizing a fastener. Alternatively, the retainer is secured to the shaft utilizing a snap-fit relationship between the retainer and the anvil assembly. The retainer, the shaft, or both, may be texturized in such a way so as to improve the frictional engagement of those parts. For example, the surface of the shaft is mechanically treated, or the shaft, the retainer, or both, have a coating that increases friction between the shaft and the retainer.

The anvil assembly may include a hub attached to the anvil member. In certain embodiments, the surgical stapling instrument has a tubular body portion, the staple cartridge assembly being mountable in the tubular body portion; the tubular body portion has a rod, the shaft of the anvil assembly being attachable to the shaft. In certain embodiments, the surgical stapling instrument has a handle assembly.

BRIEF DESCRIPTION OF THE DRAWINGS

An embodiment or embodiments of the presently disclosed surgical instrument and staple line reinforcement material is disclosed with reference to the drawings, wherein:

FIG. 13 is a perspective view of a staple line reinforcement material in accordance with a further embodiment of the present disclosure;

FIG. 14 is perspective view of a linear surgical stapling instrument according to another embodiment of the present disclosure;

DETAILED DESCRIPTION

Figure 1:
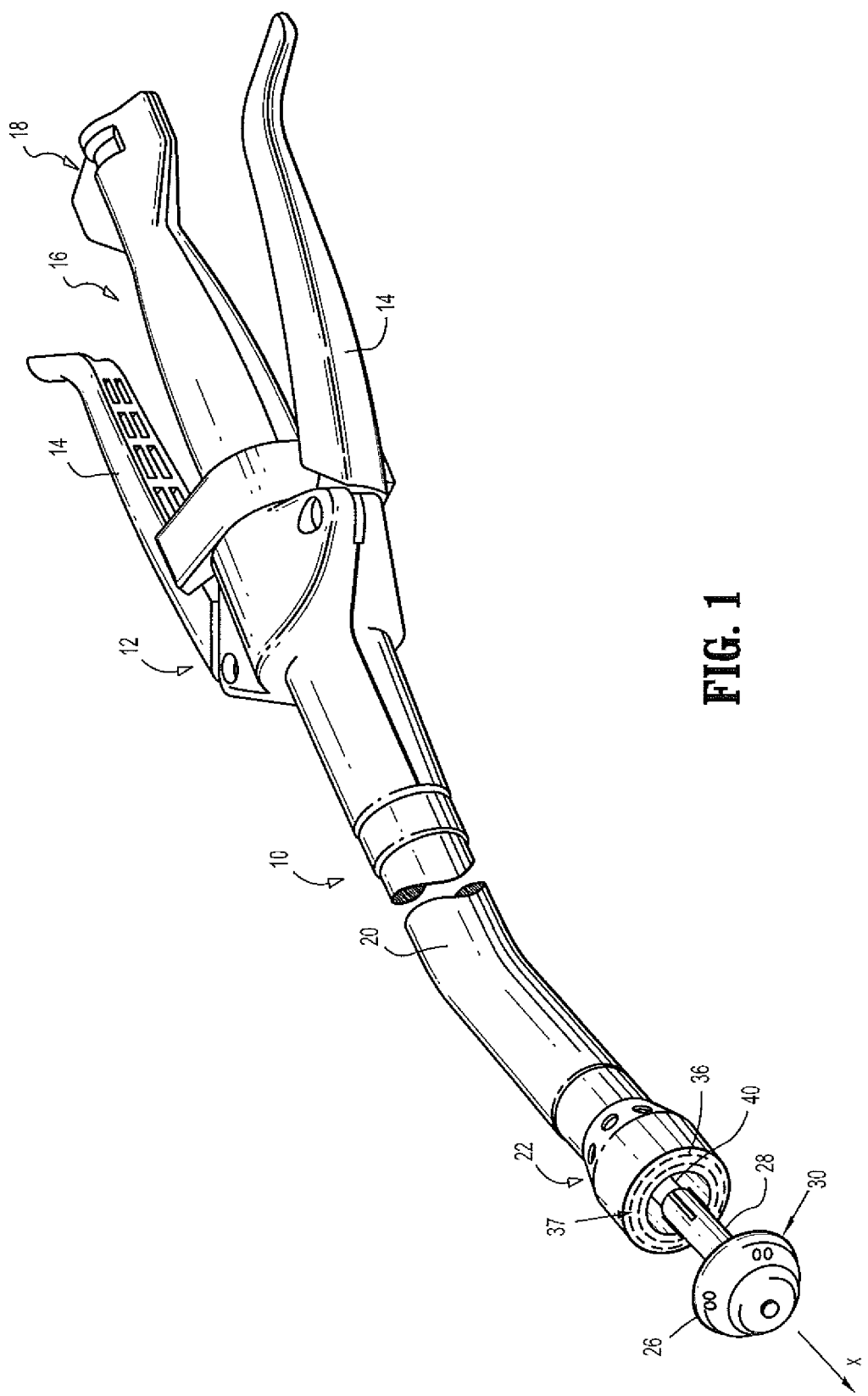
FIG. 1 is a perspective view of an embodiment of the present disclosure showing including a circular stapling instrument.

An embodiment or embodiments of the presently disclosed stapling instrument, retainer, and staple line reinforcement material will now be described in detail with reference to the drawings. Like numerals in the drawings designate identical or corresponding elements in each of the several views. As is common in the art, the term "proximal" refers to that part or component that is closer to the user of the instrument while the term "distal" refers to that part or component that is farther from the user of the instrument.

FIG. 1 illustrates a circular surgical stapling instrument which is generally designated as 10. Surgical stapling instrument 10 includes a handle assembly 12 having at least one pivotable actuating handle 14 and a rotatable actuator 18. A tubular body portion 20 extends from the handle assembly 12. The tubular body portion 20, which generally has a circular cross-sectional shape, may have a straight or a curved shape along its length and may be flexible or relatively rigid. Cross-sectional shapes other that circular are contemplated, so that the tubular body portion 20 can have a polygonal, elliptical, semi-circular, ovoid, or other shape. The body portion 20 terminates in a staple cartridge assembly 22 which includes a distally facing tissue contacting surface defining one or more rows 37 of staple receiving slots 36. Each staple receiving slot has a staple (not shown) disposed therein. Typically, a pair of circular rows 37 of staple receiving slots 36 is provided, although other shapes, such as annular, are contemplated. An anvil assembly 30 is positioned distally of the staple cartridge assembly 22, which includes an anvil member 26 and an anvil shaft 28 operatively associated therewith. The anvil assembly has a proximally facing tissue contacting surface that defines staple forming recesses 27 that correspond to the circular rows of staple receiving slots. The tubular body portion 20 has a corresponding rod or shaft 40 centrally located with respect to the staple cartridge assembly 22. The shaft 28 of the anvil assembly is removably connectable to the rod or shaft 40 of the tubular body portion 20. The anvil shaft defines a longitudinal axis "x".

The staple cartridge assembly 22 is connectable to the distal end of tubular body portion 20 or may be configured to concentrically fit within the distal end of tubular body portion 20. Typically, staple cartridge assembly 22 includes a staple pusher (not shown) with a distal portion defining two concentric rings of peripherally spaced fingers (not shown), each one of which is received within a respective staple receiving slot 36. Typically, a knife (not shown) having a cutting edge is disposed within the staple cartridge assembly 22. The knife edge is circular and disposed radially inward of the rows of staples. The knife is mounted so that as the staple pusher is advanced axially in the direction of the anvil assembly, the knife is also advanced axially. Alternatively, the knife may be separately actuated. The staple pusher is advanced in the distal direction to drive staples from the staple receiving slots 36 against the anvil member so that the staple forming recesses 27 form the staples in a closed shape. The knife is advanced and driven toward the anvil assembly 30 to cut tissue. U.S. Pat. No. 5,915,616 to Viola et al., the entire content of which is hereby incorporated herein by reference, discloses a circular stapling instrument. Although a circular stapling instrument is shown in FIG. 1, the stapling device may be arranged to deploy staples in a semi-circular, linear, or other desired shape. Although discussed with reference to intestinal tissue, devices according to the present disclosure can be arranged to join and/or treat other tissues in other procedures.

The anvil member 26 may or may not be pivotable about the anvil shaft 28 from a first, initial position in which a plane defined by the tissue contact surface 52 of the anvil member 26 is substantially perpendicular to the longitudinal axis of the anvil shaft 28 to a second position, tilted with respect to the longitudinal axis "x". The second position is desirably a reduced profile position in which anvil member 26 defines an angle with respect to the longitudinal axis "x". Alternately, the anvil member 26 is rigidly attached to the anvil shaft 28.

The anvil shaft 28 is dimensioned to releasably engage an anvil retainer (not shown) on the rod or shaft 40 of a circular surgical stapling instrument, such as the surgical stapling instrument 10. One such surgical stapling device having an anvil retainer and with which anvil assembly 30 may be used is disclosed in U.S. provisional patent application Ser. No. 60/281,259, filed Apr. 3, 2001, ("the '259 application") which is hereby incorporated by reference herein, in its entirety. The anvil retainer functions to align anvil assembly 30 with the body portion 20 (FIG. 1) of the surgical stapling instrument 10 during movement of the anvil assembly 30 from a positioned spaced from the staple cartridge assembly 22 of the surgical stapling device to an approximated position in close alignment with the staple cartridge assembly 22.

Figure 2:
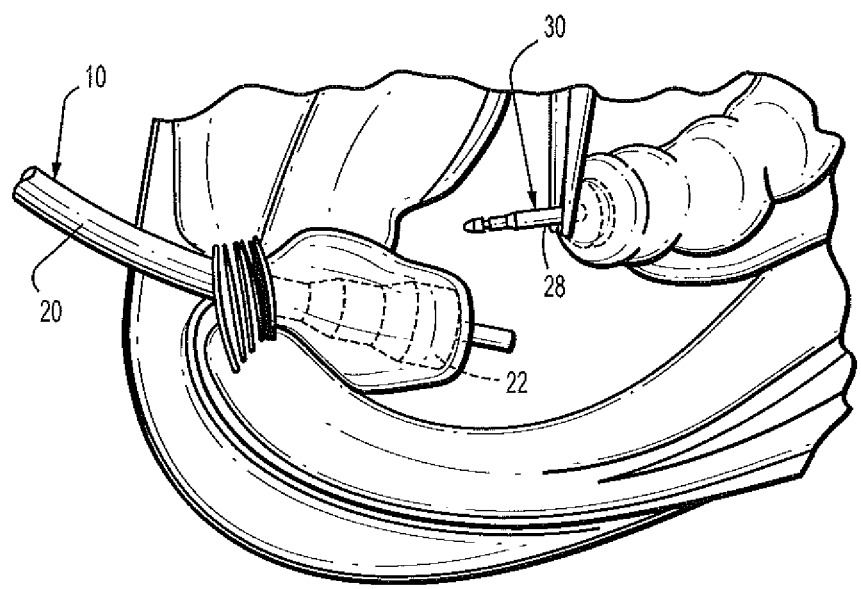
FIG. 2 is perspective view of the circular stapling instrument of FIG. 1 with the anvil assembly detached.
Figure 3:
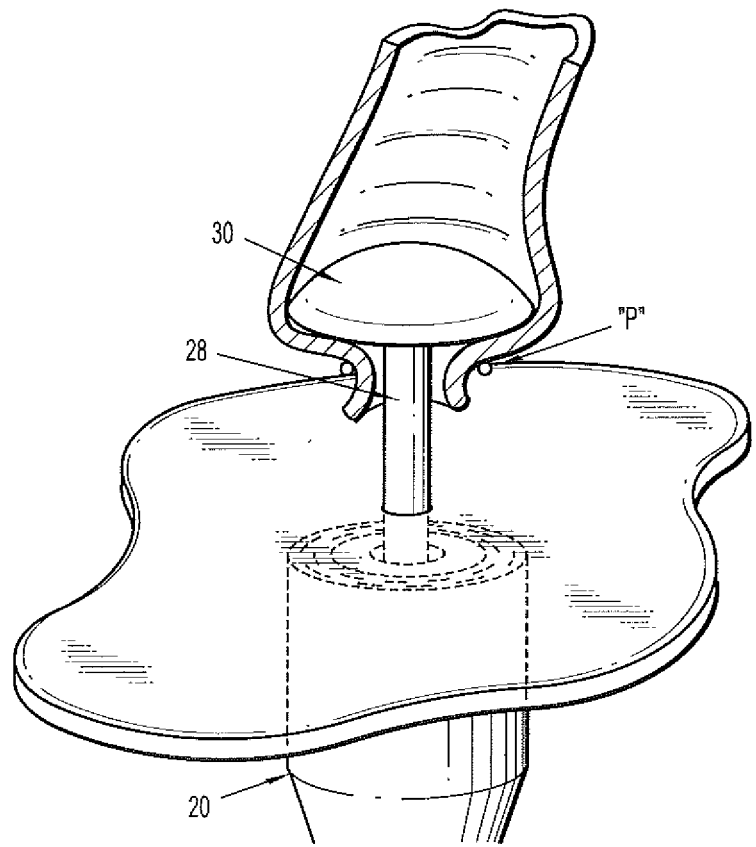
FIG. 3 is a perspective view of the circular stapling instrument of FIGS. 1 and 2 with the anvil assembly attached.

The circular stapling instrument can be used to form an anastomosis between sections of intestinal tissue. As shown in FIGS. 2 and 3, the anvil assembly 30 is detached from the rod or shaft 40 of the tubular body portion 20 and a section of tubular body vessel, such as a section of intestine, is secured to the anvil assembly 30, typically by tying a suture "P" around the shaft 28 of the anvil assembly 30. Another section of tubular tissue is secured to the tubular body portion 20 by tying a suture around the shaft 40. See FIG. 2. The shaft 28 is then connected to the shaft 40. The actuator 18 is rotated to withdraw the shafts 28, 40 thereby approximating the anvil assembly 30 with the staple cartridge assembly 22. To fire the staples, the actuating handles 14 are squeezed, which advances the staple pusher and the knife (not shown). The staples pass through each section of tubular tissue and are formed against the anvil so that the sections of tubular tissue are joined to one another. The knife cuts the tissue radially inward of the rows of staples, and the sutured material is removed with the circular stapling device.

Figure 4:
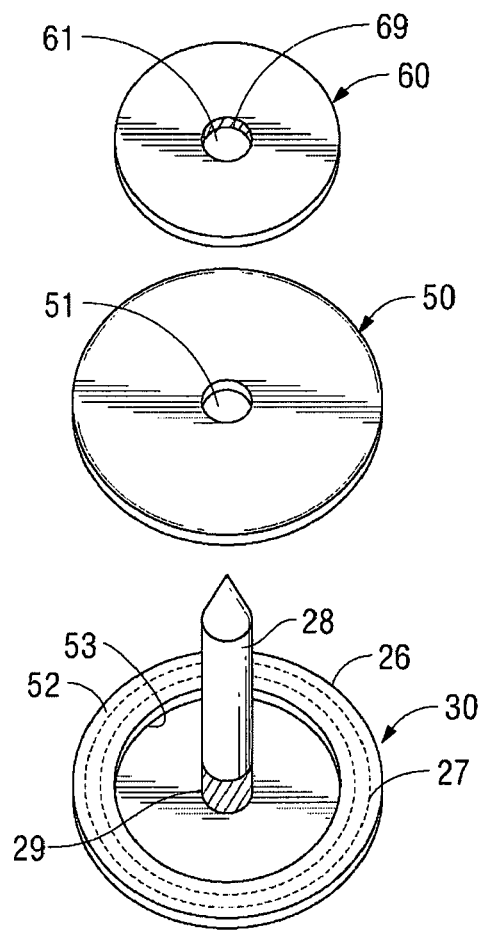
FIG. 4 is a perspective view of a circular stapling instrument anvil assembly, staple line reinforcement material, and retainer, with parts separated, according to the embodiment of FIGS. 1 through 3.
Figure 5:
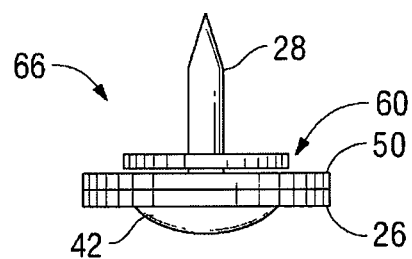
FIG. 5 is an elevation view of a staple line reinforcement material retainer assembly according to the embodiment of FIGS. 1 through 4.
Figure 6:
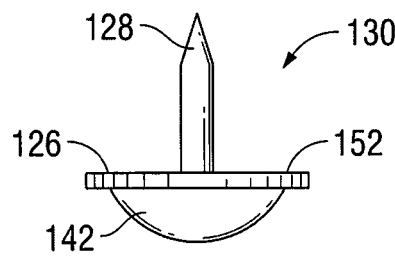
FIG. 6 is a staple line reinforcement material retainer assembly according to a further embodiment of the present disclosure.

According to the present disclosure, a surgical stapling instrument has a staple line reinforcement material retained thereon. In certain embodiments, the anvil head 42 has an inner recess 53 that is generally annular and may include a cut ring for receiving the knife. As shown in FIG. 4, a staple line reinforcement material 50 has a central aperture 51 for receiving the anvil shaft 28 and is dimensioned so that the staple line reinforcement material overlies the staple forming recesses 27 of the anvil member 26 when the staple line reinforcement material is placed on the shaft 28. A small amount of excess material may lie over the outside edge of the anvil member. A retainer 60, which may be shaped as a washer with a central aperture 61, has an outside diameter slightly less than the inside diameter of the knife so that the retainer does not interfere with cutting. The inside diameter is dimensioned to receive the anvil shaft and be frictionally retained on the shaft. FIG. 5 shows the staple line reinforcement material retainer assembly 66. When the staple line reinforcement material is placed on the anvil shaft 28 and the retainer 60 is then placed on the anvil shaft 28 over the staple line reinforcement material, the frictional engagement between the retainer 60 and the shaft keep the staple line reinforcement material in place during use. The retainer 60 may be formed of a material that has a desired coefficient of friction with the shaft, which is normally metal, such as stainless steel.

In another embodiment, the retainer is secured to the anvil assembly utilizing a fastener (such as a screw or bolt), a clip, a detent, or by a snap-fit relationship between the retainer and the anvil assembly. In a further alternative, the retainer 60, the shaft 28, or both, may be texturized 69, 29, respectively, in such a way so as to improve the frictional engagement of those parts. This can include mechanically treating the surfaces of the shaft and/or retainer, or can include coatings.

During use, the rotatable actuator 18 is manipulated to approximate the anvil assembly 30 toward the staple cartridge assembly 22 and clamp tissue therebetween. When the pivotable actuating handle 14 is moved, the knife and/or pusher will be moved in a direction toward the anvil assembly to fire the staples and cut tissue. The staple line reinforcement material retainer assembly 66 is arranged so that the retainer 60 lies inwardly of the knife. The retainer retains the staple line reinforcement material 50 against the tissue contacting surface 52 of the anvil member 26. The knife will cut the tissue and the staple line reinforcement material, making the retainer easy to remove with the circular stapling instrument 10.

Figure 7:
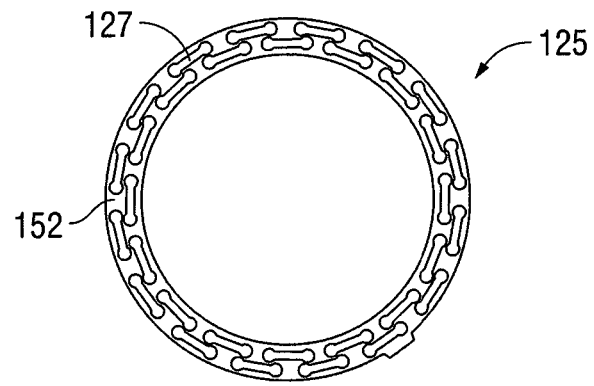
FIG. 7 is a plan view of a prior art circular stapling instrument anvil member.
Figure 8:
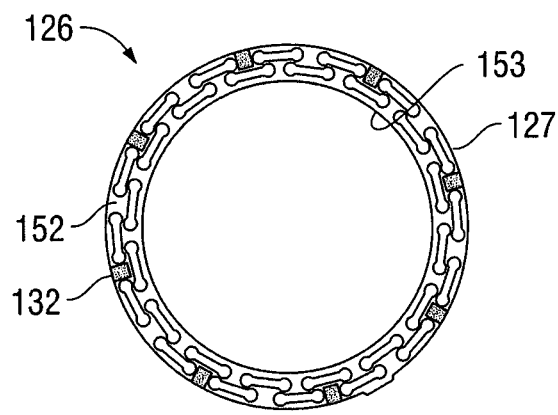
FIG. 8 is a plan view of a circular stapling instrument anvil member according to a further embodiment of the present disclosure.
Figure 10:
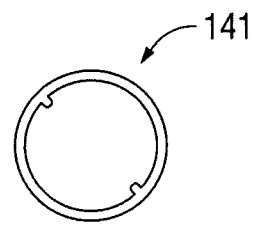
FIG. 10 is a plan view of a ring having attachment member tabs in accordance with a further embodiment of the present disclosure.

In another embodiment of the present disclosure, a circular stapling instrument as discussed above in connection with FIGS. 1 through 3 has an anvil assembly 130 with an anvil member 126 attached to an anvil head 142. The anvil assembly 130 further includes an anvil shaft 128 attachable to the rod or shaft 40. A typical prior art anvil member 125 is shown in FIG. 7 and has two rows of staple forming recesses 127 formed in the tissue contact surface 152 of the anvil member 125. An anvil member 126 according to an embodiment of the present disclosure is shown in FIG. 8. Attachment members 132, which may be formed as tabs, are attached to the anvil member 126 so that the attachment members 132 are generally flush with the tissue contact surface 152. Recessed or protruding attachment members are also contemplated. In this way, the anvil member 126 can be formed from a material that is useful for defining staple forming recesses therein and for forming staples. Thus, typically the anvil member is formed from a metal such as stainless steel. The attachment members 132 are formed from a material that is useful for attachment to a staple line reinforcement material. The staple line reinforcement material 50 is attached to the attachment members utilizing adhesives, ultrasonic or other kinds of welding, or other methods. The attachment member or members 132 may be formed of a variety of polymeric materials, such as the polymeric materials from which the staple line reinforcement material is made. In one example, recesses are formed in the anvil member, as by grinding, drilling, machining, etc. A polymeric material is overmolded on the anvil member so that attachment members of the polymeric material are disposed in the recesses. In a further embodiment, a plastic frame or ring 141 having tabs extending inwardly (see FIG. 10) is attached to the anvil member, either before or after the assembly of the anvil member 126 with the anvil head 142. The tabs are snapped into place in preformed recesses in the anvil member. Alternately, the frame or ring 141 is attached to the anvil member so that the tab or tabs are disposed adjacent the tissue contact surface 152 but outside of the staple forming recesses 127. In another embodiment, the plastic ring may be used, without tabs, so that the staple line reinforcement material is attached at the ring.

Figure 9:
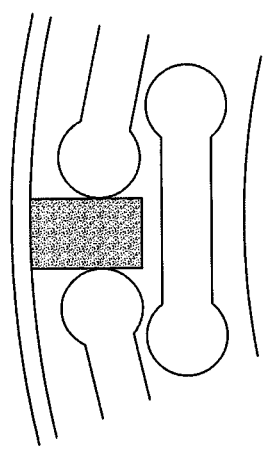
FIG. 9 is a detail of FIG. 7 showing attachment tabs.

One or more attachment members 132 may be used and they may have a variety of shapes. The tabs shown in FIG. 9 are generally trapezoidal in shape and are disposed between the staple forming recesses of the anvil member as shown in FIG. 8. The attachment members/tabs do not interfere with the formation of the staples in the staple receiving recesses.

Figure 11:
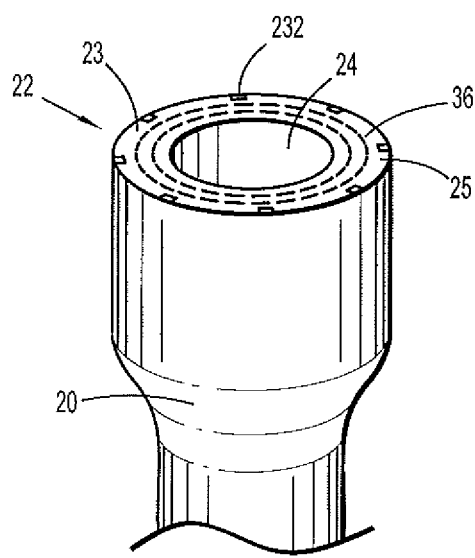
FIG. 11 is a partial perspective view of a circular stapling instrument body portion and cartridge assembly in accordance with another embodiment.
Figure 12:
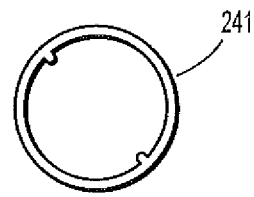
FIG. 12 is a plan view of a ring having attachment member tabs in accordance with the embodiment of FIG. 11.
Figure 15:
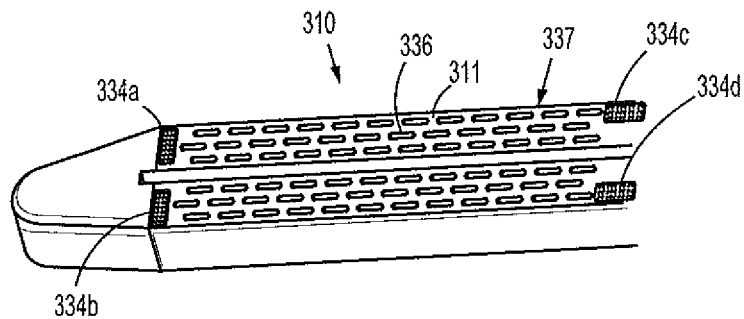
FIG. 15 is a perspective view of a staple cartridge assembly in accordance with the embodiment of FIG. 14.

It may be desirable to attach a staple line reinforcement material 50 adjacent the staple cartridge assembly 22. As shown in FIG. 11, the staple cartridge assembly 22 has a central recess 24 through which the rod or shaft 40 (which has been omitted for clarity) passes. An attachment member or attachment members 232, which may be formed as tabs, are attached to the tissue contact surface 25 of the cartridge assembly 22. The attachment members 232 may be formed so that they are generally flush with the tissue contact surface 25, but recessed or protruding attachment members are contemplated. The attachment member or members are formed from a material useful for attachment to the staple line reinforcement material. The staple line reinforcement material 50 is attached to the attachment members utilizing adhesives, ultrasonic or other kinds of welding, or other methods. The attachment members 232 may be formed from a variety of polymeric materials, such as the polymeric materials from which the staple line reinforcement material is made. In one example, recesses are formed in the staple cartridge tissue contact surface 25 and a polymeric material is overmolded on the staple cartridge in the recesses. In this way, the material of the staple cartridge can be different from the material for attaching the staple line reinforcement material. In other embodiment, a plastic frame or ring 241 (FIG. 11) having tabs extending inwardly is attached to the staple cartridge so there the tabs are snapped into place in preformed recesses. Alternately, the frame or ring 241 is attached to the cartridge assembly or to the body portion 20 so that the tab or tabs are disposed on the tissue contact surface 25 but lie outwardly of the staple slots 36. In another embodiment, the plastic ring may be used, without tabs, so that the staple line reinforcement material is attached at the ring.

Alternately, the material of the staple cartridge 23, which is normally plastic, can be selected so as to be useful for attaching the staple line reinforcement material by adhesives, ultrasonic or other kinds of welding, or other methods. In certain embodiments, the anvil assembly 130 includes a cut ring disposed in the recess 153. The cut ring can be formed with tabs extending proximally toward the tissue contact surface 152 so as to be accessible for attachment to the staple line reinforcement material.

In the embodiments discussed in connection with FIGS. 6 through 12, the staple line reinforcement material 50 can be dimensioned to have an inner diameter that is smaller than the diameter of the knife of the circular stapling instrument. When the knife is actuated, a portion of the staple line reinforcement material is removed. This may tend to increase the firing forces for the circular stapling instrument. Alternately, the staple line reinforcement material 50 can be dimensioned to have an inner diameter that is larger than the diameter of the knife of the circular stapling instrument so that the knife does not cut the staple line reinforcement material. When the staple firing is actuated, the staples hit the staple line reinforcement material, passing through the staple line reinforcement material. The staples that impact near the weld or other attachment points apply enough force to substantially break the connection between the staple line reinforcement material and the attachment member or attachment members. The staple line reinforcement material is thereby released. Alternately, the gentle manipulation of the circular stapling instrument can be relied upon to gently separate the staple line reinforcement material from the attachment points.

Figure 19:
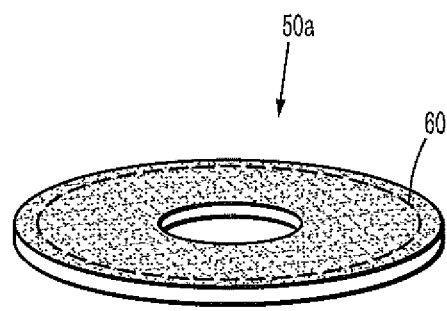
FIG. 19 is a perspective view of a staple line reinforcement material in accordance with an embodiment of the present disclosure.

In another embodiment of the present disclosure, a surgical stapling instrument and staple line reinforcement material according to FIGS. 1 through 3 and 6 through 12 has a staple line reinforcement material 50a attached to an attachment member or attachment members 132 disposed at the tissue contacting surface 52 of the anvil assembly and/or disposed at the tissue contact surface 25 of the staple cartridge assembly 22. The attachment member or members 132 are formed from a material that is useful for attaching the staple line reinforcement material 50a. The staple line reinforcement material 50a is attached to the attachment member or attachment members 132 permanently, so that the material 50 is not intended to be releasable when the staples are fired or the instrument is manipulated in removing the instrument from the surgical site. The staple line reinforcement material includes perforations 68, or areas of weakness, adjacent the attachment member or members. See FIG. 19. The inner diameter of the staple line reinforcement material 50a is larger than the diameter of the knife. Desirably, the attachment member or attachment members 132 lie outwardly of the staple forming recesses 27 of the anvil assembly 30 and/or outwardly of the staple receiving slots 36 of the staple cartridge assembly 22. The perforations 68 are disposed inwardly of the attachment member or members 132, but outwardly of the knife. In use, the anvil assembly will be approximated with the staple cartridge assembly to clamp tissue, and the staples will be fired and the knife deployed. Upon removal of the stapling instrument, the staple line reinforcement material 50a will separate from the anvil assembly and/or cartridge assembly at the perforations. A margin of material will remain with the anvil assembly and/or cartridge assembly.

In another embodiment, the staple line reinforcement material 50a has an inner diameter that is smaller than the diameter of the knife so that a portion of the staple line reinforcement material 50a is severed removed by the knife.

In another embodiment of the present disclosure a linear stapling instrument is used with a staple line reinforcement material on the anvil, the cartridge assembly, or both. The linear stapling instrument 300 has stapler jaws 310, 320. See FIG. 14. The stapler jaw 310 is a staple cartridge assembly having one or more rows 337 of staple receiving slots 336. Each staple receiving slot has a staple (not shown) disposed therein. Typically, three linear rows 337 of staple receiving slots 336 are provided on either side of a channel 339. The other jaw is an anvil assembly 320 positioned in opposition to the staple cartridge assembly 310 and pivotably mounted so that the anvil assembly and staple cartridge assembly can be approximated to clamp tissue therebetween. The anvil assembly includes an anvil member 326 defining a plurality of staple forming recesses 331 that correspond to the linear rows 337 so that the stapling instrument forms linear staple lines. The stapling jaws 310, 320 are disposed at a distal end of an endoscopic shaft 340. A handle assembly 301 includes a pivotable handle 303 that drives movement of a drive member through the staple cartridge assembly 310. The drive member (not shown) passes through the channel 339 and pushes a sled or camming bar through the staple cartridge to drive staple pushers, and the staples, through the slots 336 toward the staple forming recesses of the anvil member 326. Certain embodiments of such a surgical instrument is disclosed in U.S. Pat. No. 6,241,139 to Milliman et al., the disclosure of which is hereby incorporated by reference herein, in its entirety.

Figure 16:
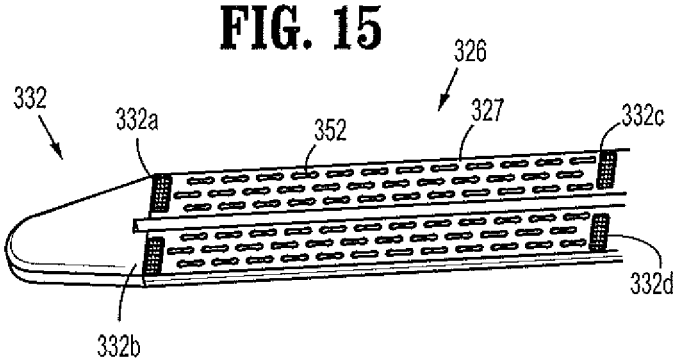
FIG. 16 is a perspective view of an anvil member in accordance with the embodiment of FIGS. 14 through 15.
Figure 17:
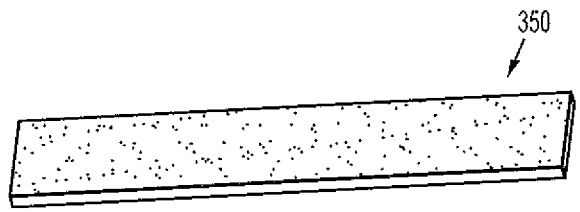
FIG. 17 is a perspective view of a staple line reinforcement material in accordance with the embodiment of FIGS. 14 through 16.

To attach the staple line reinforcement material to the jaw or jaws 310, 330, attachment members are formed on or in the cartridge assembly 310 and/or anvil assembly 330. Typically the anvil member 326 is formed from a metal such as stainless steel. The attachment members 332 are formed from a material that is useful for attachment to a staple line reinforcement material. The staple line reinforcement material 350 is attached to the attachment members 332 utilizing adhesives, ultrasonic or other kinds of welding, or other methods. The attachment member or members 332 may be formed of a variety of polymeric materials, such as the polymeric materials from which the staple line reinforcement material is made. In one example, recesses are formed in the anvil member, as by grinding, drilling, machining, etc. A polymeric material is overmolded on the anvil member so that attachment members of the polymeric material are disposed in the recesses. In one embodiment, the attachment members 332 include a first distal attachment member 332a, a second distal attachment member 332b, a first proximal attachment member 332c, and a second proximal attachment member 332d, so that there are one or more attachment members at each of the distal and proximal ends of the anvil member. See FIG. 16.

Figure 18:
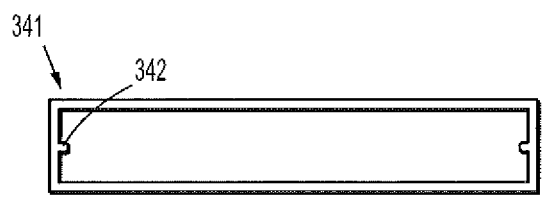
FIG. 18 is a plan view of a ring or frame having attachment member tabs in accordance with the embodiment of FIGS. 14 through 17.

In a further embodiment, a plastic frame or ring 341 having tabs 342 extending inwardly (see FIG. 18) is attached to the anvil member, either before or after the assembly of the anvil member 326 in the anvil assembly. The tabs are snapped into place in preformed recesses in the anvil member. Alternately, the frame or ring 341 is attached to the anvil member so that the tab or tabs are disposed adjacent the tissue contact surface 352 but outside of the staple forming recesses 327. In another embodiment, the plastic frame or ring may be used, without tabs, so that the staple line reinforcement material is attached at the ring.

It may be desirable to attach a staple line reinforcement material to the tissue contact surface 311 of the cartridge assembly 310. Attachment members 334 are provided for the staple cartridge assembly and are formed from a material that is useful for attachment to a staple line reinforcement material. The staple line reinforcement material 350 is attached to the attachment members 334 utilizing adhesives, ultrasonic or other kinds of welding, or other methods. The attachment member or members 334 may be formed of a variety of polymeric materials, such as the polymeric materials from which the staple line reinforcement material is made. The attachment member or members 334 can be made by providing recesses in the tissue contact surface 311 of the cartridge assembly 310, and overmolding. Alternately, a plastic frame or ring, like that shown in FIG. 18 may or may not include tabs and provides a surface at which to attach the staple line reinforcement material using adhesives, ultrasonic or other welding, and other methods. Alternatively, the material of the staple cartridge can be selected so as to be useful for attaching the staple line reinforcement material.

Figure 20:
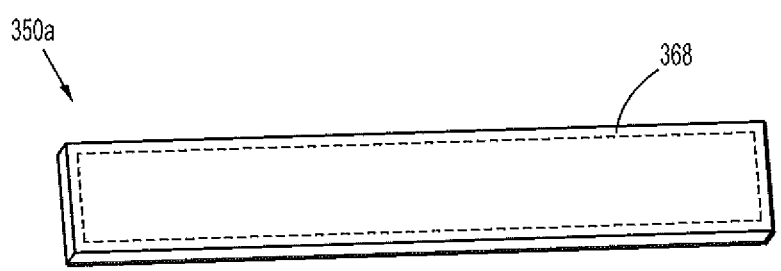
FIG. 20 is a perspective view of a staple line reinforcement material in accordance with a further embodiment of the present disclosure.

In another embodiment of the present disclosure, a surgical stapling instrument and staple line reinforcement material according to FIGS. 14 through 18 has a staple line reinforcement material 350A attached to an attachment member or attachment members 332 disposed at the tissue contacting surface of the anvil assembly 320 and/or attachment member or members 334 disposed at the tissue contact surface of the staple cartridge assembly 310. The attachment member or members 332, 334 are formed from a material that is useful for attaching the staple line reinforcement material 350A. The staple line reinforcement material 350A is attached to the attachment member or attachment members 332, 334 permanently, so that the material 350A is not intended to be releasable when the staples are fired or the instrument is manipulated in removing the instrument from the surgical site. The staple line reinforcement material includes perforations 368, or areas of weakness, adjacent the attachment member or members 332, 334. See FIG. 20. Desirably, the attachment member or attachment members 332, 334 lie outwardly of the rows 337 of staple forming recesses 331 of the anvil assembly 30 and/or outwardly of the rows 337 of the staple receiving slots 336 of the staple cartridge assembly 310. The perforations are disposed inwardly of the attachment member or members 332, 334, but outwardly of the rows 337 staple forming recesses 331 of the anvil assembly 30 and/or outwardly of the rows 337 of the staple receiving slots 336. In use, the anvil assembly will be approximated with the staple cartridge assembly to clamp tissue, and the staples will be fired and the knife deployed. Upon removal of the stapling instrument, the staple line reinforcement material 350A will separate from the anvil assembly and/or cartridge assembly at the perforations. A margin of staple line reinforcement material remains with the surgical stapling instrument.

It is contemplated that the staple line reinforcement materials discussed above may be fabricated from or include a surgical grade, biocompatible, non-absorbable material and may comprise a mesh. For example, the staple line reinforcement material may be fabricated from "TEFLON", which is a registered trademark owned by DuPont de Nemours & Co. It is further contemplated that body portion 102 may be fabricated from a biocompatible polymeric foam, felt, polytetrafluoroethylene (ePTFE), gelatin, fabric or the like, or any other biocompatible material.

Non-absorbable materials used for staple line reinforcement material include, and are not limited to, those that are fabricated from such polymers as polyethylene, polypropylene, nylon, polyethylene terephthalate, polytetrafluoroethylene, polyvinylidene fluoride, and the like. Further non-absorbable materials include and are not limited to stainless steel, titanium and the like.

In one embodiment, the staple line reinforcement material may be fabricated from a bio-absorbable material. In other embodiments, the staple line reinforcement material has at least one portion that is absorbable and at least one portion that is not absorbable. Bio-absorbable materials used for staple line reinforcement material include, and are not limited to, those fabricated from homopolymers, copolymers or blends obtained from one or more monomers selected from the group consisting of glycolide, glycolic acid, lactide, lactic acid, p-dioxanone, α-caprolactone and trimethylene carbonate. Other bio-absorbable materials include and are not limited to, for example, Polyglycolic Acid (PGA) and Polylactic Acid (PLA). In one embodiment, the staple line reinforcement material may be fabricated from bio-absorbable felt, gelatin or any other bio-absorbable materials.

The staple line reinforcement material can incorporate a wound treatment material, which includes and is not limited to one or a combination of adhesives, hemostats, sealants, coagulants, astringents, and medicaments. Other surgically biocompatible wound treatment materials which may be employed in or applied by surgical instruments, including surgical staplers, include adhesives whose function is to attach or hold organs, tissues or structures; sealants to prevent fluid leakage; hemostats to halt or prevent bleeding; coagulants, astringents (e.g., sulfates of aluminum) and medicaments. Examples of adhesives which can be employed include protein derived, aldehyde-based adhesive materials, for example, the commercially available albumin/ glutaraldehyde materials sold under the trade designation BioGlue™ by Cryolife, Inc., and cyanoacrylate-based materials sold under the trade designations Indermil™ and Derma Bond™ by Tyco Healthcare Group, LP and Ethicon Endosurgery, Inc., respectively. Examples of sealants, which can be employed, include fibrin sealants and collagen-based and synthetic polymer-based tissue sealants. Examples of commercially available sealants are synthetic polyethylene glycol-based, hydrogel materials sold under the trade designation CoSeal™ by Cohesion Technologies and Baxter International, Inc. Examples of hemostat materials, which can be employed, include fibrin-based, collagen-based, oxidized regenerated cellulose-based and gelatin-based topical hemostats. Examples of commercially available hemostat materials are fibrinogen-thrombin combination materials sold under the trade designations CoStasis™ by Tyco Healthcare Group, LP, and Tisseel™ sold by Baxter International, Inc. The wound treatment material can include medicaments. Medicaments may include one or more medically and/or surgically useful substances such as drugs, enzymes, growth factors, peptides, proteins, dyes, diagnostic agents or hemostasis agents, monoclonal antibodies, or any other pharmaceutical used in the prevention of stenosis.

The staple line reinforcement material may include a single layer including a homogeneous array of bio-absorbable or non-absorbable materials or a heterogeneous array of bio-absorbable and/or non-absorbable materials. The staple line reinforcement material may include a layered body portion having at least two layers as indicated by first layer, film or wafer and second layer, film or wafer. In this embodiment, each layer may include a homogeneous or heterogeneous array of bio-absorbable and/or non-absorbable materials.

In certain preferred embodiments, the staple line reinforcement material is a non-woven fabric. The non-woven fabric can be formed utilizing a melt blown process, including the following steps. The polymer resin is melt extruded. A melt pump meters out the molten polymer to a die head having an array of holes. By way of example, the holes have a diameter of between about 0.175 and about 0.25 millimeters. The polymer is forced through the array of holes in the die. Polymer fibers exit the die and are forced onto a conveyor belt. A stream of blowing hot air can be used to force the polymer fibers onto the conveyor. Suction through the conveyor belt surface can be used to compact the fibers against the belt and against each other, as the fibers cool. Additional compression may be applied to the fibers, such as by using a calendaring roll, which may include heating or cooling. The non-woven fabric may then be annealed. For example, isometric tension or other uniform compression can be used to drive crystallization and remove the monomer. The polymer is desirably a bioabsorbable or non-bioabsorbable polymer, such as a glycolide lactide copolymer (the material utilized in Polysorb™ sutures), a termpolymer composed of glycolide, trimethylene carbonate and dioxanone (the material utilized in Biosyn™ sutures), a polymer of glycolide, caprolactone, trimethylene carbonate, and lactide (the material utilized in Caprosyn™ sutures), and a glycolide trimethylene carbonate copolymer (the material utilized in Maxon™ sutures).

In certain embodiments, the non-woven fabric is porous. For example, the non-woven fabric can have a porosity of between about 50% and about 90%. The fiber diameter may be between about 5 and about 100 µm. The fabric thickness may be between about 150 and about 400 µm.

It will be understood that various modifications may be made to the embodiments disclosed herein. For example, the surgical stapling instrument need not apply staples but rather may apply two part fasteners as is known in the art. Further, the length of the linear row of staples or fasteners, or the length or diameter of a circular row of staples or fasteners, may be modified to meet the requirements of a particular surgical procedure. Therefore, the above description should not be construed as limiting, but merely as exemplifications of preferred embodiments. Those skilled in the art will envision other modifications within the scope and spirit of the claims appended thereto.

What is claimed is:

1. A surgical stapling instrument, comprising:
   an anvil assembly having a tissue contacting surface defining a plurality of rows of staple forming recesses therein, wherein each pair of adjacent staple forming recesses of a first row of the plurality of rows of staple forming recesses defines a gap therebetween;
   a staple cartridge assembly having a tissue contacting surface defining a plurality of rows of staple receiving slots therein, wherein each pair of adjacent staple receiving slots of a first row of the plurality of rows of staple receiving slots defines a gap therebetween; and
   a plurality of attachment members supported on the tissue contacting surface of at least one of the staple cartridge assembly or the anvil assembly, the plurality of attachment members disposed in every other of the gaps in the first row of the plurality of rows of staple forming recesses or in every other of the gaps in the first row of the plurality of rows of staple receiving slots, wherein the plurality of attachment members is configured to be attached to a staple line reinforcement material; wherein the plurality of attachment members are hook and loop type fasteners.

2. The surgical stapling instrument according to claim 1, wherein the gap of a first pair of adjacent staple receiving slots of the first row of the plurality of rows of stapling receiving slots has a first attachment member of the plurality of attachment members disposed therein, and the gap of a second pair of adjacent staple receiving slots of the first row of the plurality of rows of stapling receiving slots is devoid of an attachment member, the first and second pairs of adjacent staple receiving slots being disposed adjacent one another.

3. The surgical stapling instrument according to claim 2, wherein the gap of a third pair of adjacent staple receiving slots of the first row of the plurality of rows of stapling receiving slots has a second attachment member of the plurality of attachment members disposed therein, the second pair of adjacent staple receiving slots being disposed between the first and third pairs of adjacent staple receiving slots.

4. The surgical stapling instrument according to claim 1, wherein the gap of a first pair of adjacent staple forming recesses of the first row of the plurality of rows of stapling forming recesses has a first attachment member of the plurality of attachment members disposed therein, and the gap of a second pair of adjacent staple forming recesses of the first row of the plurality of rows of stapling forming recesses is devoid of an attachment member, the first and second pairs of adjacent staple forming recesses being disposed adjacent one another.

5. The surgical stapling instrument according to claim 4, wherein the gap of a third pair of adjacent staple forming recesses of the first row of the plurality of rows of stapling forming recesses has a second attachment member of the plurality of attachment members disposed therein, the second pair of adjacent staple forming recesses being disposed between the first and third pairs of adjacent staple forming recesses.

6. The surgical stapling instrument according to claim 1, wherein the plurality of rows of staple receiving slots are arranged in an annular array, and wherein the first row of the plurality of rows of staple receiving slots is a radially outermost row of the plurality of rows of staple receiving slots.

7. The surgical stapling instrument according to claim 6, wherein a second row of the plurality of rows of stapling receiving slots, radially inward of the first row of staple receiving slots, is devoid of attachment members.

8. The surgical stapling instrument according to claim 1, wherein the plurality of rows of staple forming recesses are arranged in an annular array, and wherein the first row of the plurality of rows of staple forming recesses is a radially outermost row of the plurality of rows of staple forming recesses.

9. The surgical stapling instrument according to claim 8, wherein a second row of the plurality of rows of stapling forming recesses, radially inward of the first row of staple forming recesses, is devoid of attachment members.

10. The surgical stapling instrument according to claim 1, wherein the plurality of rows of staple receiving slots and the plurality of rows of staple forming recesses are annular.

* * * * *